US012076705B2

(12) United States Patent
Whittaker et al.

(10) Patent No.: US 12,076,705 B2
(45) Date of Patent: Sep. 3, 2024

(54) CAPTURE OF FLUORINATED CARBON COMPOUNDS

(71) Applicant: The University of Queensland, St Lucia (AU)

(72) Inventors: Andrew Whittaker, Toowong (AU); Cheng Zhang, Calamvale (AU); Xiao Tan, St. Lucia (AU)

(73) Assignee: The University of Queensland, St Lucia (AU)

( * ) Notice: Subject to any disclaimer, the term of this patent is extended or adjusted under 35 U.S.C. 154(b) by 443 days.

(21) Appl. No.: 17/429,217

(22) PCT Filed: Feb. 7, 2020

(86) PCT No.: PCT/AU2020/050104
§ 371 (c)(1),
(2) Date: Aug. 6, 2021

(87) PCT Pub. No.: WO2020/160626
PCT Pub. Date: Aug. 13, 2020

(65) Prior Publication Data
US 2022/0126270 A1    Apr. 28, 2022

(30) Foreign Application Priority Data
Feb. 8, 2019  (AU) ................................ 2019900400

(51) Int. Cl.
*B01J 20/26*   (2006.01)
*A61M 1/36*   (2006.01)
(Continued)

(52) U.S. Cl.
CPC .......... *B01J 20/264* (2013.01); *A61M 1/3679* (2013.01); *C02F 1/285* (2013.01);
(Continued)

(58) Field of Classification Search
CPC .. B01J 20/264; B01J 20/3204; B01J 20/3276; B01J 2220/44; A61M 1/3679;
(Continued)

(56) References Cited

U.S. PATENT DOCUMENTS

2012/0025414 A1*  2/2012  Schmidt ................. G01N 33/92
                                                                  425/130
2015/0136690 A1*  5/2015  Xie ........................ B01D 71/06
                                                                  427/244
(Continued)

FOREIGN PATENT DOCUMENTS

CN   105745318 B  *  6/2012  ............. B01D 21/26
JP   2014-231056       12/2014
(Continued)

OTHER PUBLICATIONS

Koda et al Publication: "Fluorous Microgel Star Polymers: Selective Recognition and Separation of Polyfluorinated Surfactants and Compounds in Water", Journal of the American Chemical Society, pp. 15742-15748, Published Oct. 10, 2014. (Year: 2014).*
(Continued)

*Primary Examiner* — Joseph W Drodge
(74) *Attorney, Agent, or Firm* — Nixon & Vanderhye P.C.

(57) ABSTRACT

The present invention describes a method of capturing a fluorinated carbon compound located within a liquid, the method comprising contacting the fluorinated carbon compound with a block copolymer having a backbone comprising a hydrophilic block and a fluoropolyether block, wherein the fluorinated carbon compound binds to and is captured by the block copolymer.

21 Claims, 12 Drawing Sheets

(51) Int. Cl.
*C02F 1/28* (2023.01)
*C02F 1/58* (2023.01)
*C08F 290/00* (2006.01)
*C08F 290/06* (2006.01)
*C02F 101/14* (2006.01)
*C02F 101/36* (2006.01)

(52) U.S. Cl.
CPC .......... *C02F 1/583* (2013.01); *C08F 290/062* (2013.01); *C02F 2101/14* (2013.01); *C02F 2101/363* (2013.01)

(58) Field of Classification Search
CPC ....... A61M 1/3687; C02F 1/285; C02F 1/583; C02F 2101/14; C02F 2101/363; C02F 2101/12; C02F 2101/36; C08F 290/062; C08F 293/005; C08F 2438/03; B01D 15/00; B01D 15/36; B01D 2257/2066; B01D 69/147; B01D 71/26; B01D 71/38; B01D 71/52
See application file for complete search history.

(56) References Cited

U.S. PATENT DOCUMENTS

| | | | | |
|---|---|---|---|---|
| 2016/0199785 | A1* | 7/2016 | Kumar | B01D 67/0009 523/310 |
| 2016/0288060 | A1* | 10/2016 | Aamer | B01D 69/10 |
| 2019/0351373 | A1* | 11/2019 | Kumar | B01D 71/80 |
| 2019/0351374 | A1* | 11/2019 | Kumar | B01D 69/105 |

FOREIGN PATENT DOCUMENTS

| | | | |
|---|---|---|---|
| JP | 2014-231056 A | 12/2014 | |
| WO | 2013/164287 | 11/2013 | |
| WO | 2015/041119 | 3/2015 | |
| WO | WO2019004298 A1 * | 1/2019 | ............ B01D 61/04 |

OTHER PUBLICATIONS

McCleaf et al Publication: Removal efficiency of multiple poly- and perfluoroalkyl substances (PFASs) in drinking water using granulated activated carbon (GAC) and anion exchange (AE) column tests, Water Research, vol. 120, pp. 77-87, Published 2017. (Year: 2017).*
English Translation of Campton et al Publication CN105745318B, published Jun. 2018. (Year: 2018).*
English Translation of Itakura et al Publication WO2019004298A1, published Jan. 2019. (Year: 2019).*
Saleh et al Publication: Removal of poly- and per-fluoroalkyl substances from aqueous systems by nano-enabled water treatment strategies, Environmental Science Water Research & Technology, vol. 5, pp. 198-208, Published Feb. 1, 2019. (Year: 2019).*
International Search Report for PCT/AU2020/050104 mailed Apr. 15, 2020, 4 pages.
Written Opinion of the ISA for PCT/AU2020/050104 mailed Apr. 15, 2020, 4 pages.
Extended European Search Report dated Dec. 8, 2022, issued in European Application No. 20752232.7, 8 pages.
Moonshi, Shehzahdi S., et al., "A unique 19F Mri agent for the tracking of non phagocytic cells in vivo", Nanoscale, vol. 10, No. 17, 2018, pp. 8226-8239.

* cited by examiner

CAPTURE OF FLUORINATED CARBON COMPOUNDS

This application is the U.S. national phase of International Application No. PCT/AU2020/050104 filed Feb. 7, 2020 which designated the U.S. and claims priority to AU Patent Application No. 2019900400 filed Feb. 8, 2019, the entire contents of each of which are hereby incorporated by reference.

FIELD OF THE INVENTION

The present invention relates in general to fluorinated carbon compounds. In particular, the invention relates to capturing fluorinated carbon compounds located within a liquid.

BACKGROUND OF THE INVENTION

Fluorinated carbon compounds, also known as organofluorine compounds, contain one or more carbon-fluorine covalent bonds. A carbon-fluorine covalent bond is particularly strong and imparts a high degree of stability to such compounds.

Fluorinated carbon compounds are known for their chemical stability, chemical resistance and heat resistance, to name but a few of their advantageous properties. Such advantageous properties have seen wide application of such compounds in both household and industrial settings.

While the stability of fluorinated carbon compounds makes them particularly useful in numerous applications, that property also renders the compounds persistent in the environment in that they are not readily degraded.

Significant environmental concern is now emerging not only in terms of the persistence of such compounds in the environment, but also their bioaccumulation in both animals and humans.

Of perhaps most concern is mounting evidence that some classes of fluorinated carbon compounds are toxic to living organisms. Furthermore, fluorinated carbon compounds such as per- and polyfluoroalkyl substances (PFAS) have a significant half-life in the human body.

Considerable research has consequently been directed toward developing techniques for removing fluorinated carbon compounds from the environment.

Fluorinated carbon compounds may persist in the environment either being associated with solid or liquid matter.

Techniques for remediating solid matter, for example soil, contaminated fluorinated carbon compounds are known. Such techniques include desorption of the compounds from the solid matter using heat.

The removal of fluorinated carbon compounds from liquid matter has proven more complex. Techniques developed to date include extraction/adsorption with activated carbon or anionic exchange resins, extraction using membrane filtration/reverse osmosis, and extraction through precipitation/flocculation.

Despite having an ability to remove fluorinated carbon compounds from liquids, techniques developed to date can be rather complex and inefficient. Furthermore, they are typically restricted to remediating wastewater.

Accordingly, there remains an opportunity to develop a technique for remediating liquids contaminated with fluorinated carbon compounds that addresses one or more problems associated with prior art techniques or at the least provides a useful alternative.

SUMMARY OF THE INVENTION

The present invention provides a method of capturing a fluorinated carbon compound located within a liquid, the method comprising contacting the fluorinated carbon compound with a block copolymer having a backbone comprising a hydrophilic block and a fluoropolyether block, wherein the fluorinated carbon compound binds to and is captured by the block copolymer.

Surprisingly, it has now been found block copolymers used in accordance with the invention present an advantageous ability to rapidly and selectively adsorb at high capacity fluorinated carbon compounds within a liquid environment. The adsorbed fluorinated carbon compound in effect binds with the block copolymer and can be readily removed from the liquid simply by separating the block copolymer from the liquid. The selectivity, adsorption rate and capacity of the block copolymer for fluorinated carbon compounds are superior to that which can be achieved using conventional technology.

The block copolymer used in accordance with the invention surprisingly provides such advantageous properties in various liquid environments ranging from, for example, aqueous liquids (e.g. wastewater) to blood products.

Fluorinated carbon compounds bound to the block copolymer can be readily released by treatment with organic solvent and/or through the application of heat. Such release of the fluorinated carbon compound from the block copolymer advantageously enables (i) the fluorinated carbon compound to be collected/concentrated, and (ii) the block copolymer to be recycled in further application of capturing fluorinated carbon compounds.

The method according to the present invention therefore represents a highly efficient and effective means for capturing and removing fluorinated carbon compounds located within a liquid.

In one embodiment, the fluoropolyether block of the block copolymer presents polyether functionality in the block copolymer backbone.

In another embodiment, the fluoropolyether block of the block copolymer presents polyether functionality pendant to the block copolymer backbone.

In another embodiment, the hydrophilic block of the block copolymer presents hydrophilic functionality pendant to the block copolymer backbone.

In yet a further embodiment, the hydrophilic block of the block copolymer presents hydrophilic functionality in the block copolymer backbone.

In one embodiment, the fluoropolyether block of the block copolymer is a perfluoropolyether block.

In a further embodiment, the fluorinated carbon compound comprises per and/or poly-fluoroalkyl substance (PFAS).

In yet a further embodiment, the fluorinated carbon compound is selected from one or more of perfluoromethyl cyclohexane, perfluorohexane, perfluorooctane, methyl pentadecafluoroheptyl ketone, methyl pentadecafluorooctanoate, perfluorohexane sulfonate, perfluorooctanoic acid, perfluorooctane sulfonate, perfluorooctanoic acid ammonium salt, perfluorohexanoic acid, perfluorononanoic acid, perfluorodecanoic acid, perfluorododecanoic acid perfluorooctanesulfonic acid, and potassium perfluorooctanesulfonate.

In another embodiment, the fluorinated carbon compound is selected from one or more of perfluorohexane sulfonate, perfluorooctanoic acid and perfluorooctane sulfonate.

In one embodiment, the fluorinated compound is located within an aqueous liquid, for example wastewater.

In another embodiment, the fluorinated compound is located within a blood product.

The method according to the present invention may further comprise a step of removing the fluorinated carbon compound from the liquid by separating from the liquid the block copolymer having the fluorinated carbon compound bound thereto.

In yet another embodiment, after removing the fluorinated carbon compound from the liquid, the fluorinated carbon compound bound to the block copolymer may be separated from the block copolymer. In one embodiment, the fluorinated carbon compound is separated from the block copolymer by adding an organic solvent to the block copolymer having the fluorinated carbon compound bound thereto. Alternatively, the fluorinated carbon compound may be separated from the block copolymer by heating the block copolymer having the fluorinated carbon compound bound thereto. Heating may be performed at temperatures of at least 40° C., or at least 50° C., or at least 60° C., or at least 70° C.

In one embodiment, the hydrophilic block of the block copolymer comprises a polyoxyalkylene moiety.

In yet another embodiment, the block copolymer is covalently bound to a solid substrate.

The present invention also provide use of a block copolymer for capturing a fluorinated carbon compound located within a liquid, the block copolymer having a backbone comprising a hydrophilic block and a fluoropolyether block.

Further aspects and/or embodiments are discussed in more detail below.

BRIEF DESCRIPTION OF THE DRAWINGS

The following invention will herein be described with reference to the following non-limiting drawings in which.

DETAILED DESCRIPTION OF THE INVENTION

Figure 1:
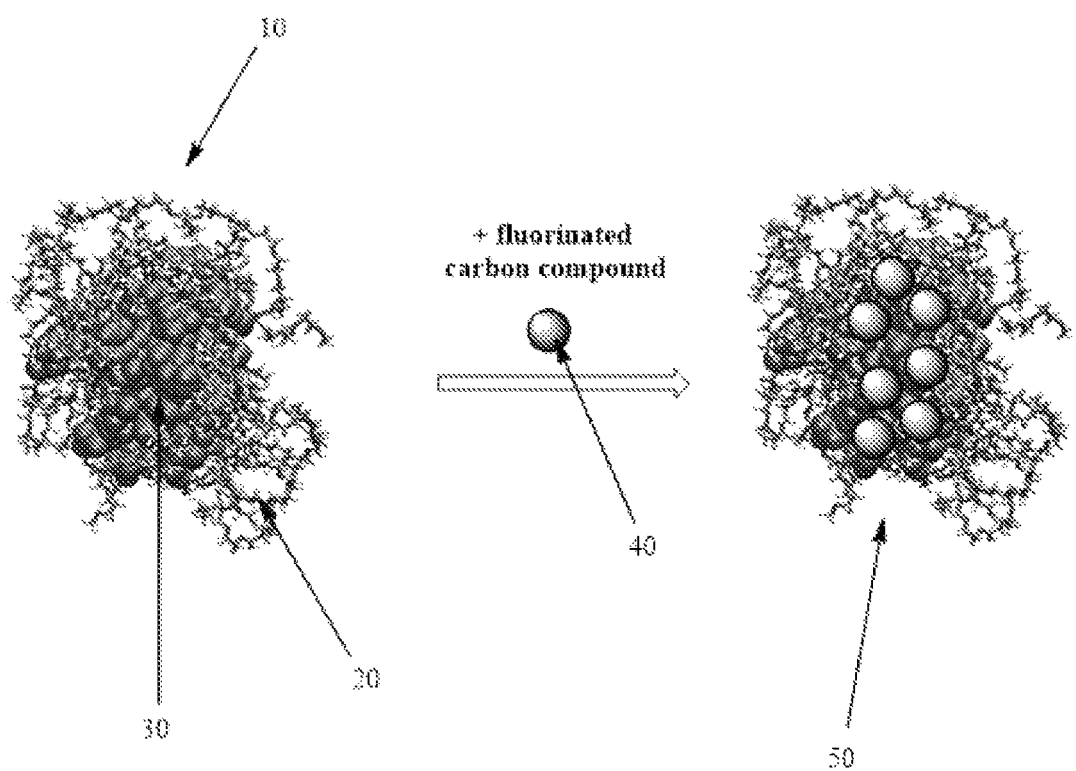
FIG. 1 illustrates fluorinated carbon compound binding to a block copolymer according to the method of the invention.

The present invention relates to a method of capturing a fluorinated carbon compound located within the liquid.

By "capturing" the fluorinated carbon compound is meant freedom of the compound within the liquid is restrained by the block copolymer. In the context of the present invention, and as will be discussed in detail below, the fluorinated compound is captured by a block copolymer in the sense the fluorinated carbon compound binds to the block copolymer.

As will also be discussed in more detail below, capturing the fluorinated carbon compound in the manner described advantageously facilitates removing the compound from the liquid.

Reference herein to a "fluorinated carbon compound" is intended to mean a hydrocarbon compound in which one or more hydrogen atoms have been substituted with a fluorine atom. Generally, the fluorinated carbon compound will contain multiple fluorine atoms. Fluorinated carbon compounds are also known in the art as organofluorine compounds.

Common fluorinated carbon compounds relevant to the present invention include per- and poly-fluoroalkyl substances (PFAS).

Examples of fluorinated carbon compounds include fluoroalkanes, fluorinated alkyl and aryl halides, fluorochloroalkenes, fluoroethers and epoxides, fluoroalcohols, fluoroamines, fluoroketones, fluorocarboxylic acids, fluoronitriles and isonitriles, fluorosulfonic acids, perfluoroalkanes, perfluorinated alkyl and aryl halides, perfluoroethers and epoxides, perfluoroalcohols, perfluoroamines, perfluoroketones, perfluorocarboxylic acids, perfluoronitriles and isonitriles, perfluorosulfonic acids.

More specific examples of fluorinated carbon compounds include fluoromethyl cyclohexane, fluorohexane, fluorooctane, methyl pentadecafluoroheptyl ketone, fluorohexane sulfonate, fluorooctanoic acid, fluorooctane sulfonate, fluorooctanoic acid ammonium salt, fluorohexanoic acid, fluorononanoic acid, fluorodecanoic acid, fluorododecanoic acid fluorooctanesulfonic acid, and potassium fluorooctanesulfonate.

Other specific examples of fluorinated carbon compounds include perfluoromethyl cyclohexane, perfluorohexane, perfluorooctane, methyl pentadecafluoroheptyl ketone, methyl pentadecafluorooctanoate, perfluorohexane sulfonate, perfluorooctanoic acid, perfluorooctane sulfonate, perfluorooctanoic acid ammonium salt, perfluorohexanoic acid, perfluorononanoic acid, perfluorodecanoic acid, perfluorododecanoic acid perfluorooctanesulfonic acid, and potassium perfluorooctanesulfonate.

The fluorinated carbon compounds to be captured in accordance with the invention are located within a liquid. By being "located" within a liquid is meant the fluorinated carbon compound is either dissolved or suspended within the liquid. The liquid may also be described as comprising fluorinated carbon compound.

The method according to the invention can advantageously be performed when the fluorinated carbon compound is located within various types of liquids.

In one embodiment, the fluorinated carbon compound is located within an aqueous liquid.

In the context of a liquid within which the fluorinated carbon compound is located, the expression "aqueous liquid" is intended to mean at least 50 vol %, at least 60 vol %, at least 70 vol %, at least 80 vol %, at least 90 vol %, at least 95 vol %, or at least 98 vol % of water. The aqueous liquid may comprise one or more other components, such as aqueous soluble liquids, for example methanol, ethanol and tetrahydrofuran (THF).

Examples of aqueous liquids include, potable water and wastewater such as industrial wastewater, for example fire training waste water.

In a further embodiment, the fluorinated carbon compound is located within a liquid blood product.

Suitable blood products may include, but are not limited to, whole blood, washed blood and cell-free serum.

Fluorinated carbon compound captured in accordance with the invention may and often will be a contaminant in a liquid that is in need remediation. For example, the fluorinated carbon compound may be present in industrial wastewater or in a blood product.

There is no particular limitation on the means by which the fluorinated carbon compound located within the liquid comes to be in that a liquid. For example, the fluorinated compound may be inherently present in groundwater, industrial wastewater or a blood product.

Alternatively, liquid may be deliberately contaminated with the fluorinated carbon compound for the purpose of that liquid subsequently being remediated using the method of the invention to remove the fluorinated carbon compound from the liquid.

For example, solid matter such as soil/dirt/earth/ground/clay (conveniently herein simply referred to as soil) comprising (e.g. contaminated) with fluorinated carbon compound may be subjected to an extraction process and provide for liquid comprising fluorinated carbon compound. The so formed liquid having fluorinated carbon compound located therein may then be used in accordance with the method of the invention. Such an extraction process could be applied, for example, as part of a heap leaching process to afford leachate having fluorinated compound located therein.

In one embodiment, the liquid having fluorinated carbon compound located therein is obtained by a process comprising contacting a liquid with solid matter comprising fluorinated carbon compound.

In a further embodiment, the liquid having fluorinated carbon compound located therein is a leachate from a heap leaching process.

In another embodiment, the liquid having fluorinated carbon compound located therein is obtained by a process comprising extracting fluorinated carbon compound from soil using a liquid.

The method according to the invention comprises contacting the fluorinated carbon compound with the block copolymer. The method step of contacting the fluorinated carbon compound with the block copolymer may be achieved by any suitable means. For example, the block copolymer may be added to the liquid in which the fluorinated carbon compound is located. Alternatively, the liquid in which the fluorinated carbon compound is located may be added to the block copolymer.

The block copolymer itself will typically also be located within a liquid.

Accordingly, the method step of contacting the fluorinated carbon compound with the block copolymer may involve combining the liquid in which the fluorinated carbon compound is located with a liquid in which the block copolymer is located.

If required, stirring may be implemented to facilitate contact between the fluorinated carbon compound with the block copolymer.

Surprisingly, the method according to the invention can be implemented with little or no stirring to facilitate contact between the fluorinated carbon compound and the block copolymer. Without wishing to be limited by theory, the ability to perform the invention with little or no stirring is believed to stem from one or more of the unique fast adsorption rate, high capacity and high selectivity of the block copolymer for the fluorinated carbon compounds.

Contacting the fluorinated carbon compound with the block copolymer can be performed using equipment well known to those skilled in the art. For example, conventional mixing vessels may be employed. The contacting step may be performed batch wise or as part of a continuous process.

The block copolymer used in accordance with the invention has a backbone comprising a hydrophilic block and a fluoropolyether block.

As used herein, the expression "block copolymer" is intended to mean a copolymer having two or more polymer chains (or blocks) that are chemically different and covalently attached to each other. In the context of the present invention the block copolymer has a hydrophilic block covalently attached to a fluoropolyether block.

The "backbone" of the block copolymer represents the main chain of its molecular structure.

The backbone of the block copolymer comprises a hydrophilic block.

By the backbone of the block copolymer having a hydrophilic block is meant a section or region of the copolymer (i.e. a block) that exhibits overall hydrophilic character. By having "hydrophilic" character is meant the hydrophilic block, if isolated, would be soluble in an aqueous liquid. For the purpose of determining such hydrophilic character, the expression "aqueous liquid" is intended to mean at least 50 vol %, at least 60 vol %, at least 70 vol %, at least 80 vol %, at least 90 vol %, at least 95 vol %, or at least 98 vol % of water. The aqueous liquid may comprise one or more other components, such as aqueous soluble liquids, for example methanol, ethanol and tetrahydrofuran (THF).

The hydrophilic block will itself be polymeric or oligomeric.

The hydrophilic block that forms part of the block copolymer will generally be prepared by polymerising a monomer composition that comprises hydrophilic monomer.

As a guide only, examples of hydrophilic monomers that may be used in preparing the hydrophilic block include, but are not limited to, alkylene oxides, alkylene glycols, and ethylenically unsaturated monomers such as acrylic acid, methacrylic acid, hydroxyethyl methacrylate, hydroxypropyl methacrylate, oligo(alkylene glycol) methylether(meth)acrylate, acrylamide and methacrylamide, hydroxyethyl acrylate, N-methylacrylamide, N,N-dimethylacrylamide, N,N-dimethylaminoethyl methacrylate, N,N-dimethylaminopropyl methacrylamide, N-hydroxypropyl methacrylamide, 4-acryloylmorpholine, 2-acrylamido-2-methyl-1-propanesulfonic acid, N-vinylpyrolidone, oligo(2-methyl-2-oxazoline) (meth)acrylate, oligo(2-ethyl-2-oxazoline) (meth)acrylate, oligo(2-(n-propyl)-2-oxazoline) (meth)acrylate, and 2-(methylsulfinyl)ethyl acrylate In one embodiment, the hydrophilic block comprises a polyoxyalkylene moiety.

Examples of suitable polyoxyalkylene moieties include those comprising an oxyalkylene group of formula: —O(CR$^X$R$^Y$)$_i$—, where R$^X$ and R$^Y$ are each independently selected from hydrogen and optionally substituted alkyl, and i is an integer ranging from 1 to 10, for example 1 to 8, or from 1 to 6, or from 1 to 4. Generally, R$^X$ and R$^Y$ are each independently selected from hydrogen and optionally substituted C$_{1-6}$ alkyl, and i is an integer selected from 2, 3, and 4. When i>1, each (CR$^X$R$^Y$) may be the same or different. For example, when the oxyalkylene unit is an oxyethylene unit, R$^X$ and R$^Y$ are both hydrogen and i=2 (i.e. —O(CH$_2$)$_2$—), and where the oxyalkylene unit is an oxypropylene unit, i=2 and R$^X$ and R$^Y$ of the first "i" are both hydrogen and R$^X$ and R$^Y$ of the second "i" can respectively be hydrogen and methyl (i.e. —OCH$_2$CH(CH$_3$)—).

Each oxyalkylene group or unit within the polyoxyalkylene may be the same or different. In other words, the polyoxyalkylene may be a homopolymer or a copolymer (including a random or block copolymer). The oxyalkylene units may be derived, for example, from an alkylene oxide such as ethylene oxide, propylene oxide, or butylene oxide.

In one embodiment, the hydrophilic block comprises an oxyethylene group, an oxypropylene group or a combination thereof.

The hydrophilic block (in isolation) will generally have a number average molecular weight ranging from about 1,000 to about 100,000 g/mol.

The number-average molecular weight (M$_n$) and molecular weight distribution (molar mass dispersity, Đ=M$_w$/M$_n$) of the polymers are those determined by SEC using a Waters Alliance 2690 separation module equipped with a Waters 2414 differential refractive index (RI) detector, a Waters 2489 UV/vis detector, a Waters 717 Plus autosampler, and a Waters 1515 isocratic HPLC pump. THF was used as the mobile phase with a flow rate of 1 mL/min. The system is calibrated using polystyrene standards with molecular weights ranging from 6.82×10$^2$ to 1.67×10$^6$ g/mol. The polymers are dissolved in THF, filtered through a PTFE membrane (0.45 μm pore size), and then subjected to injection.

The hydrophilic block will comprise hydrophilic moiety or functionality that imparts overall hydrophilic character to the hydrophilic block. The hydrophilic block may comprise other moieties or functionality that in their own right do not impart hydrophilic character per se. The hydrophilic block will be defined by a polymeric or oligomeric section or region that overall presents the required hydrophilic character.

There is no particular limitation as to the manner in which the hydrophilic block structurally presents the hydrophilic moiety/functionality (relative to the block copolymer backbone) in order to impart the required hydrophilic character.

In one embodiment, the hydrophilic block presents hydrophilic functionality pendant to the block copolymer backbone.

In a further embodiment, the hydrophilic block presents hydrophilic functionality in the block copolymer backbone.

Such molecular structural variations of the hydrophilic block are explained in further detail with reference to Scheme 1.

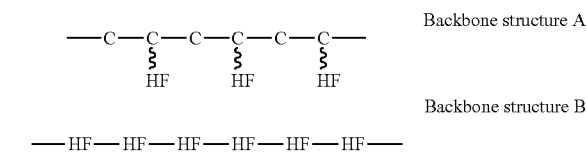

Scheme 1: Pendant hydrophilic functionality (A), and in chain hydrophilic functionality (B).

With reference to Scheme 1, structure A is a simplistic illustration of a hydrophilic block that presents hydrophilic functionality (HF) pendant to the block copolymer backbone (only part of which is shown). Structure B is a simplistic illustration of a hydrophilic block that presents the hydrophilic functionality (HF) in the block copolymer backbone (only part of which is shown).

The backbone of the block copolymer also comprises a fluoropolyether block.

By the backbone of the block copolymer comprising a fluoropolyether bock is meant a section or region of the copolymer (i.e. a block) that is replete with fluoropolyether functionality. Accordingly, the fluoropolyether block will comprise a repeat group having two or more hydrocarbon moieties linked with an oxygen atom defining the "ether" of the fluoropolyether. At least one and typically two or more of the hydrocarbon groups has at least one hydrogen atom replaced with a fluorine atom or a fluoroalkyl group.

There is no particular limitation as to the manner in which the fluoropolyether functionality structurally presents relative to the block copolymer backbone.

In one embodiment, the fluoropolyether block presents polyether functionality in the block copolymer backbone.

In another embodiment, the fluoropolyether block presents polyether functionality pendant to the block copolymer backbone.

Such molecular structural variations of the fluoropolyether block are explained in further detail with reference to Scheme 2.

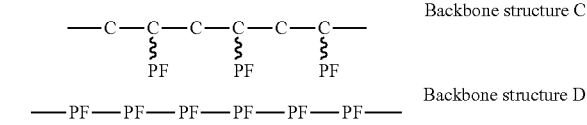

Scheme 2: Pendant polyether functionality (C), and in chain polyether functionality (D).

With reference to Scheme 2, structure C is a simplistic illustration of a fluoropolyether block that presents polyether functionality (PF) pendant to the block copolymer backbone (only part of which is shown). Structure D is a simplistic illustration of a fluoropolyether block that presents the polyether functionality (PF) in the block copolymer backbone (only part of which is shown). Those skilled in the art will of course appreciate fluoro-groups are covalently attached to the polyether functionality (not shown in Scheme 2).

In one embodiment, the fluoropolyether block is a perfluoropolyether block.

Reference herein to the expression "perfluoropolyether" in the context of the fluoropolyether block is intended to mean fluoropolyether in which all hydrogen atoms on all hydrocarbon groups are replaced with fluorine atoms.

In one embodiment, the fluoropolyether block comprises a moiety selected from —$(C_pF_{2p}O)$—, —$(CF(Z)O)$—, —$(CF(Z)C_pF_{2p}O)$—, —$(C_pF_{2p}CF(Z)O)$—, —$CF_2CF(Z)O)$—, or combinations thereof, where p is an integer ranging from 1 to 10, or 1 to 8, or 1 to 6, and where Z is selected from a fluoroalkyl group, a fluoroether group, a fluoropolyether group, or a fluoroalkoxy group.

In one embodiment, Z in the moieties outlined directly above is selected from a perfluoroalkyl group, a perfluoroether group, a perfluoropolyether group, and a perfluoroalkoxy group.

In another embodiment, the fluoropolyether block comprises a moiety selected from $C_3F_7O(CF(CF_3)CF_2O)_nCF(CF_3)$—, $C_3F_7O(CF_2CF_2CF_2O)_nCF_2CF_2$—, and $CF_3O(C_2F_4O)_nCF_2$—, where n ranges from 1 to 50, for example 3 to 30, 3 to 15, or 3 to 10.

The hydrophilic and/or fluoropolyether blocks of the block copolymer may form part of a linear, branched, hyperbranched, star or dendritic polymer structure.

In one embodiment, the block copolymer has a linear structure.

The fluoropolyether block that forms part of the block copolymer may be prepared by polymerising ethylenically unsaturated monomer that comprises fluoropolyether functionality, for example fluoroether substituted vinyl ethers, perfluoroether substituted vinyl ethers, fluoroether substituted styrenes, perfluoroether substituted styrenes, fluoroether substituted norbornyl, perfluoroether substituted norbornyl, fluoropolyether (meth) acrylates and perfluoropolyether (meth) acrylates.

The fluoropolyether block (in isolation) will generally have a number average molecular weight ranging from about 200 to about 10,000 g/mol.

Reference herein to a given block of the block copolymer having a number average molecular weight "in isolation" is intended to mean the molecular weight of that block alone as if it is not associated with any other block of the block copolymer.

The block copolymer (overall) will generally have a number average molecular weight ranging from about 1,200 to about 110,000 g/mol.

Reference to the number average molecular weight of the block copolymer "overall" is intended to mean the molecular weight of the block copolymer inclusive of both the hydrophilic and fluoropolyether blocks.

More specific examples of the block copolymer used in accordance with the invention include, but are not limited to, those comprising formula (I), (II) or (II):

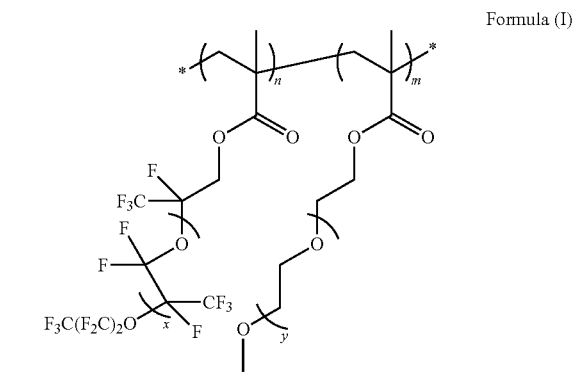

Formula (I)

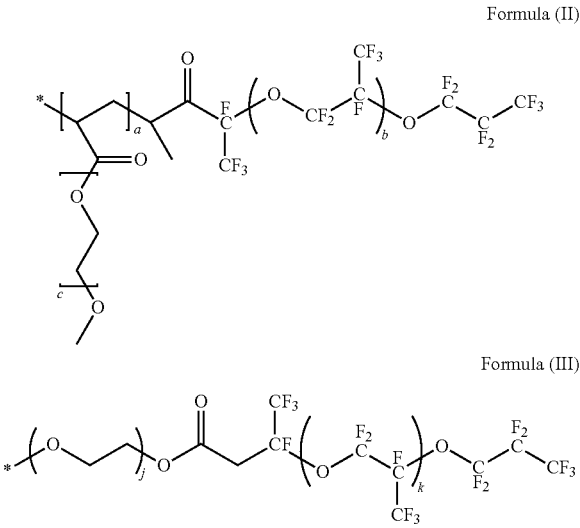

Formula (II)

Formula (III)

Where in structure (I), n is an integer ranging from 1 to about 30, m is an integer ranging from 1 to about 1000, x is an integer ranging from 1 to about 100 and y is an integer ranging from 1 to about 1000, in structure (II) a is an integer ranging from 1 to about 40, b is an integer ranging from 1 to about 100 and c is an integer ranging from 1 to about 1000, in structure (III) j is an integer ranging from 1 to about 1000 and k is an integer ranging from 1 to about 100, and wherein in structures (I), (II) and (III) * represents a covalent connection point to the remainder of the block co polymer structure.

In one embodiment, in formula (I) n is an integer ranging from 1 to about 15, m is an integer ranging from 1 to about 400, x is an integer ranging from 1 to about 50 and y is an integer ranging from about 1 to about 400.

In another embodiment, in formula (II) a is an integer ranging from 1 to about 20, b is an integer ranging from 1 to about 50 and c is an integer ranging from 1 to about 400.

In a further embodiment, in formula (III) j is an integer ranging from 1 to about 400 and k is an integer ranging from 1 to about 50.

Block copolymers used in accordance with the invention may be prepared using polymerisation techniques well known in the art.

The block copolymers may be prepared in full or in part by the polymerisation of ethylenically unsaturated monomers. Polymerisation of such ethylenically unsaturated monomers is preferably conducted using a living or a so called "quasi" living polymerisation technique.

Living or quasi living polymerisation is generally considered in the art to be a form of chain polymerisation in which irreversible chain termination is substantially absent. An important feature of living polymerisation is that polymer chains will continue to grow while monomer and reaction conditions to support polymerisation are provided. Polymer chains prepared by living polymerisation can advantageously exhibit a well defined molecular architecture, a predetermined molecular weight and narrow molecular weight distribution or low molar mass dispersity.

Examples of living polymerisation include ionic polymerisation and controlled radical polymerisation (CRP). Examples of CRP include, but are not limited to, iniferter polymerisation, stable free radical mediated polymerisation (SFRP), atom transfer radical polymerisation (ATRP), and reversible addition fragmentation chain transfer (RAFT) polymerisation.

Equipment, conditions, and reagents for performing living polymerisation are well known to those skilled in the art.

Where ethylenically unsaturated monomers are polymerised by a living polymerisation technique, it will generally be necessary to make use of a so-called living polymerisation agent. By "living polymerisation agent" is meant a compound that can participate in and control or mediate the living polymerisation of one or more ethylenically unsaturated monomers so as to form a living polymer chain (i.e. a polymer chain that has been formed according to a living polymerisation technique).

Living polymerisation agents include, but are not limited to, those which promote a living polymerisation technique selected from ionic polymerisation and CRP.

In one embodiment, the block copolymer is prepared using ionic polymerisation.

In another embodiment, the block copolymer is prepared using CRP.

In a further embodiment, the block copolymer is prepared using iniferter polymerisation.

In another embodiment, the block copolymer is prepared using SFRP.

In a further embodiment, the block copolymer is prepared using ATRP.

In yet a further embodiment, the block copolymer is prepared using RAFT polymerisation.

A polymer prepared by RAFT polymerisation may conveniently be referred to as a RAFT polymer. By virtue of the mechanism of polymerisation, such polymers will comprise residue of the RAFT agent that facilitated polymerisation of the monomer.

RAFT agents suitable for use in accordance with the invention comprise a thiocarbonylthio group (which is a divalent moiety represented by: —C(S)S—). RAFT polymerisation and RAFT agents are described in numerous publications such as WO 98/01478, Moad G.; Rizzardo, E; Thang S, H. Polymer 2008, 49, 1079-113 land Aust. J. Chem., 2005, 58, 379-410; Aust. J. Chem., 2006, 59, 669-692; and Aust. J. Chem., 2009, 62, 1402-1472. Suitable RAFT agents for use in preparing the branched polymers include xanthate, dithioester, dithiocarbamate and trithiocarbonate compounds.

Where a free radical polymerisation technique is to be used in polymerising one or more ethylenically unsaturated monomers so as to form all or part of the block copolymer, the polymerisation will usually require initiation from a source of free radicals.

A source of initiating radicals can be provided by any suitable means of generating free radicals, such as the thermally induced homolytic scission of suitable compound (s) (thermal initiators such as peroxides, peroxyesters, or azo compounds), the spontaneous generation from monomers (e.g. styrene), redox initiating systems, photochemical initiating systems or high energy radiation such as electron beam, X-ray or gamma-radiation.

Suitable initiating systems are described in commonly available texts. See, for example, Moad and Solomon "The Chemistry of Free Radical Polymerisation", Pergamon, London, 1995, pp 53-95.

Methods for preparing block copolymers suitable for use in accordance with the invention are also described in Macromolecules 2017, 50, 5953-5963, Nanoscale 10(17): 8226-8239 and ACS Nano 2018, 12, 9162-9176.

In performing the method of the invention the block copolymer may be provided in a liquid.

In one embodiment, the block copolymer is provided in an aqueous liquid. In that context, the nature of the aqueous liquid can be the same as that herein defined.

Accordingly, the method of the invention may comprise contacting the fluorinated carbon compound with the block copolymer located within a liquid, the block copolymer having a backbone comprising hydrophilic block and a fluoropolyether block.

When located within a liquid, the block copolymer may present as a unimer or an aggregate of block copolymer chains.

In one embodiment, the block copolymer is located within a liquid and presents as dispersed particles having an average hydrodynamic diameter ranging from about 5 nm to about 200 nm.

In one embodiment, the block copolymer is located within a liquid in the form of an aggregate comprising two or more block copolymer chains, for example 2 to about 5 block copolymer chains, or from 2 to about 4 block copolymer chains.

According to the method of the invention, the fluorinated carbon compound binds to and is captured by the block copolymer. Without wishing to be limited by theory, it is believed binding of the fluorinated carbon compound to the block copolymer proceeds by an adsorption process driven by interactions such as dipole forces and/or Van der Waals forces.

Surprisingly, block copolymers used in accordance with the invention have been found to exhibit excellent binding properties with fluorinated carbon compounds. In particular, the block copolymers have been found to exhibit a high rate of adsorption, a high capacity of adsorption and high selectivity for fluorinated carbon compounds.

In one embodiment, the block copolymers exhibit an adsorption capacity for fluorinated carbon compounds of at least 500, or at least 700, or at least 900, or at least 1,000 mg/g.

The adsorption capacity can be measured using quantitative $^{19}$F NMR spectroscopy.

In a further embodiment, the block copolymer exhibits a sorption equilibrium time for fluorinated carbon compounds of less than about 5 hours, or less than about 4 hours, or less than about 3 hours, or less than about 2 hours, or less than about 1 hour, or less than about 0.5 hours, or less than about 0.4 hours, or less than about 0.3 hours, or less than about 0.1 hours (h).

The block copolymers used in accordance with the invention also demonstrate excellent selectivity for fluorinated carbon compounds. Without wishing to be limited by theory, that selectivity is believed to result from fluorine atom attraction between the fluoropolyether block of the block copolymer and the fluorinated carbon compound. For example, the block copolymer has been found to exhibit little if no adsorption capacity for non-fluorinated equivalent compounds, such as octatonic acid.

The method of the inventing can be used to remediate liquid samples having a wide concentration range of fluorinated carbon compound, for example at concentrations ranging from 0.01 to 5000 µg/L.

There is not particular limitation on the amount of block copolymer that can be used in the method of the invention. The amount used will generally be dictated by the amount of fluorinated carbon compound expected to be in the liquid that is to be treated. The concentration of the block copolymer used in the method may, for example range from about 0.5 mf/ml to about 40 mg/ml.

By performing the method of the invention the fluorinated carbon compound binds to and is captured by the block copolymer. Capturing the fluorinated carbon compound in this way facilitates its removal from the liquid. Such binding of the fluorinated carbon compound may be described with reference to FIG. 1.

FIG. 1 illustrates a block copolymer (10) having a backbone comprising a hydrophilic block (20) and a fluoropolyether block (30) within a liquid (not shown). The hydrophilic block (20) presents as an outer shell and the fluoropolyether block (30) presents as an inner core. Upon contacting the block copolymer (10) with fluorinated carbon compound (40), the fluorinated carbon compound binds with the fluoropolyether block of the block copolymer (50).

In one embodiment, the method according to the invention further comprises removing the fluorinated carbon compound from the liquid by separating from the liquid the block copolymer having the fluorinated carbon compound bound thereto.

The block copolymer having the fluorinated carbon compound bound thereto can be separated from the liquid by conventional means known in the art, for example by filtration or centrifugation. As discussed below, separation from the liquid of the block copolymer having the fluorinated carbon compound bound thereto can be facilitated by having the block copolymer covalent bound to a substrate.

Once the block copolymer having the fluorinated carbon compound bound thereto has been separated from the liquid, the fluorinated carbon compound content in the liquid will of course be significantly reduced. The method of the invention can advantageous be used to reduce the concentration of fluorinated carbon compounds in a liquid to below levels recommended by heath authorities, for example to below 70 ng/L.

Having removed from the liquid the block copolymer with the fluorinated carbon compound bound thereto, the fluorinated carbon compound can itself be readily isolated.

In one embodiment, after separating from the liquid the block copolymer having the fluorinated carbon compound bound thereto, the fluorinated carbon compound and the block copolymer are separated.

Separation of the block copolymer and the fluorinated carbon compound can be achieved, for example, by contacting the block copolymer having a fluorinated carbon compound bound thereto with an organic solvent. Examples of suitable organic solvents include, but are not limited to, ethanol, methanol, tetrahydrofuran and chloroform. Alternatively, separation can be achieved by subjecting the block copolymer having the fluorinated carbon compound bound thereto to elevated temperatures, for example temperatures greater than about 40° C., or about 50° C., or about 60° C.

Upon separating the block copolymer from the fluorinated carbon compound, the block copolymer can advantageously be reused in the method according to the invention and the now isolated fluorinated carbon compound can be reused and/or disposed of in an environmentally friendly manner.

The block copolymer used in accordance with the method of the invention may be covalently bound to a solid substrate. Coupling of the block copolymer to a solid substrate may facilitate performing the method at least in the sense of enhancing the ability to separate from the liquid the block copolymer having the fluorinated carbon compound bound thereto.

There is no particular limitation on the nature of the solid substrate to which the block copolymer can be covalently bound. For example, the solid substrate may be in the form of polymer membranes or polymer beads, such as polymer beads formed from homo or copolymers of styrenic of (meth)acrylate monomers (e.g. polystyrene polymer beads). The polymer beads may be crosslinked, porous (i.e. have voids distributed throughout the bead polymer matrix) and/or also comprise solid particulate material. Such substrate bound block copolymers may be applied in the method of the invention as part of a fluidised bed, fixed bed, or cartridge filter system.

In one embodiment, the block copolymer is covalently bound to a solid substrate.

In a further embodiment, the solid substrate is a polymer bead.

In another embodiment, the polymer bead is porous.

In a further embodiment, the polymer bead comprises solid particulate material.

The solid particulate material may be of a type that results in the polymer beads having a higher density than they otherwise would have in the absence of the solid particulate material. By providing the polymer beads with an increased density, their settling time can advantageously be decreased which allows for simpler separation of the polymer beads from a liquid sample. In that case, the solid particulate material may be described as a weighting agent and assisting promoting rapid settling of the polymer beads.

According to such an embodiment, the solid particulate material used will generally be a material that has a higher density than the density of the polymer beads in the absence of the solid particulate material. The solid particulate material will typically be insoluble in any liquid that the resulting polymer beads may contact.

Examples of suitable solid particulate material include, but are not limited to, titania, zirconia, barite, cassiterite, silica, aluminosilicates, nickel oxide, copper oxide, zinc oxide, zinc sulphide, and other oxides, sulphides, sulphates, carbonates of heavy metals.

In one embodiment, the solid particulate material is a magnetic material.

As used herein, the term "magnetic" is intended to denote a property of a substance that enables it to be temporarily or permanently magnetised, and therefore includes the property of being paramagnetic. Accordingly, reference to a "magnetic particle" or a "magnetic solid particulate material" implies that this substance is at least capable of being magnetised, if not already in a magnetised state.

Incorporation of solid magnetic particulate material into the polymer beads can advantageously enable them to be used in applications involving continuous flows of liquid used in accordance with the invention. In the absence of any applied sheer, attraction between the magnetic particles in the polymer beads causes them to flocculate and settle rapidly, enabling the beads to be readily separated under more demanding process conditions.

Examples magnetic particulate material include, but are not limited to, γ-iron oxide (γ-$Fe_2O_3$, also known as maghemite), magnetite ($Fe_3O_4$), chromium dioxide, other metal oxides and more exotic magnetic materials, such as those based on neodymium or samarium and other rare earth materials, for example samarium-cobalt or neodymium iron boride. Maghemite is preferred because it is inexpensive.

The block copolymer may be covalently bound to a solid substrate by any suitable means. For example, this may include covalent attachment via specific chemical groups located at one terminus of the block copolymer. Depending on the nature of the substrate, the chemical groups may include phosphine oxide, phosphonates, carboxylates, catechols, silanes, thiols, amino groups. Those skilled in the art will be able to select suitable chemical functional groups to effect the covalent attachment depending on the nature of the substrate and block copolymer.

In one embodiment, the block copolymer is covalently bound to the solid substrate via the hydrophilic block.

The block copolymer itself may also be incorporated into a polymer matrix located on the surface of or surrounding a non-polymer solid substrate.

Terminal reactive double bonds of the block copolymer may be used to covalently bind the block copolymer into/onto the polymer matrix or polymer beads either during or after formation of the polymer matrix or polymer beads. The polymer matrix or polymer beads may porous, non-porous and/or crosslinked.

The polymer matrix or polymer beads may have additional functionality, such as capacity to be swollen by the liquid, or to absorb dissolved species such as dissolved ions. For example, the polymer matrix or polymer beads may exhibit ion exchange capacity.

In one embodiment, the block copolymer is covalently bound to a solid polymeric substrate and that polymeric substrate exhibits ion exchange capacity.

As used herein, the term "alkyl", used either alone or in compound words denotes straight chain, branched or cyclic alkyl, preferably $C_{1-20}$ alkyl, e.g. $C_{1-10}$ or $C_{1-6}$ Examples of straight chain and branched alkyl include methyl, ethyl, n-propyl, isopropyl, n-butyl, sec-butyl, t-butyl, n-pentyl, 1,2-dimethylpropyl, 1,1-dimethyl-propyl, hexyl, 4-methyl-pentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like. Where an alkyl group is referred to generally as "propyl", butyl" etc, it will be understood that this can refer to any of straight, branched and cyclic isomers where appropriate. An alkyl group may be optionally substituted by one or more optional substituents as herein defined.

The term "alkenyl" as used herein denotes groups formed from straight chain, branched or cyclic hydrocarbon residues containing at least one carbon to carbon double bond including ethylenically mono-, di- or polyunsaturated alkyl or cycloalkyl groups as previously defined, preferably $C_{2-20}$ alkenyl (e.g. $C_{2-10}$ or $C_{2-6}$). Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl. An alkenyl group may be optionally substituted by one or more optional substituents as herein defined.

As used herein the term "alkynyl" denotes groups formed from straight chain, branched or cyclic hydrocarbon residues containing at least one carbon-carbon triple bond including ethylenically mono-, di- or polyunsaturated alkyl or cycloalkyl groups as previously defined. Unless the number of carbon atoms is specified the term preferably refers to $C_{2-20}$ alkynyl (e.g. $C_{2-10}$ or $C_{2-6}$). Examples include ethynyl, 1-propynyl, 2-propynyl, and butynyl isomers, and pentynyl isomers. An alkynyl group may be optionally substituted by one or more optional substituents as herein defined.

The term "halogen" ("halo") denotes fluorine, chlorine, bromine or iodine (fluoro, chloro, bromo or iodo). Preferred halogens are chlorine, bromine or iodine.

The term "aryl" (or "carboaryl") denotes any of single, polynuclear, conjugated and fused residues of aromatic hydrocarbon ring systems (e.g $C_{6-18}$ aryl). Examples of aryl include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl. Preferred aryl include phenyl and naphthyl. An aryl group may or may not be optionally substituted by one or more optional substituents as herein defined. The term "arylene" is intended to denote the divalent form of aryl.

The term "carbocyclyl" includes any of non-aromatic monocyclic, polycyclic, fused or conjugated hydrocarbon residues, preferably $C_{3-20}$ (e.g. $C_{3-10}$ or $C_{3-8}$). The rings may be saturated, e.g. cycloalkyl, or may possess one or more double bonds (cycloalkenyl) and/or one or more triple bonds (cycloalkynyl). Particularly preferred carbocyclyl moieties are 5-6-membered or 9-10 membered ring systems. Suitable examples include cyclopropyl, cyclobutyl, cyclopentyl, cyclohexyl, cycloheptyl, cyclooctyl, cyclononyl, cyclodecyl, cyclopentenyl, cyclohexenyl, cyclooctenyl, cyclopentadienyl, cyclohexadienyl, cyclooctatetraenyl, indanyl, decalinyl and indenyl. A carbocyclyl group may be optionally substituted by one or more optional substituents as herein defined. The term "carbocyclylene" is intended to denote the divalent form of carbocyclyl.

The term "heterocyclyl" when used alone or in compound words includes any of monocyclic, polycyclic, fused or conjugated hydrocarbon residues, preferably $C_{3-20}$ (e.g. $C_{3-10}$ or $C_{3-8}$) wherein one or more carbon atoms are replaced by a heteroatom so as to provide a non-aromatic residue. Suitable heteroatoms include O, N, S, P and Se, particularly O, N and S. Where two or more carbon atoms are replaced, this may be by two or more of the same heteroatom or by different heteroatoms. The heterocyclyl group may be saturated or partially unsaturated, i.e. possess one or more double bonds. Particularly preferred heterocyclyl are 5-6 and 9-10 membered heterocyclyl. Suitable examples of heterocyclyl groups may include azridinyl, oxiranyl, thiiranyl, azetidinyl, oxetanyl, thietanyl, 2H-pyrrolyl, pyrrolidinyl, pyrrolinyl, piperidyl, piperazinyl, morpholinyl, indolinyl, imidazolidinyl, imidazolinyl, pyrazolidinyl, thiomorpholinyl, dioxanyl, tetrahydrofuranyl, tetrahydropyranyl, tetrahydropyrrolyl, tetrahydrothiophenyl, pyrazolinyl, dioxalanyl, thiazolidinyl, isoxazolidinyl, dihydropyranyl, oxazinyl, thiazinyl, thiomorpholinyl, oxathianyl, dithianyl, trioxanyl, thiadiazinyl, dithiazinyl, trithianyl, azepinyl, oxepinyl, thiepinyl, indenyl, indanyl, 3H-indolyl, isoindolinyl, 4H-quinolazinyl, chromenyl, chromanyl, isochromanyl, pyranyl and dihydropyranyl. A heterocyclyl group may be optionally substituted by one or more optional substituents as herein defined. The term "heterocyclylene" is intended to denote the divalent form of heterocyclyl.

The term "heteroaryl" includes any of monocyclic, polycyclic, fused or conjugated hydrocarbon residues, wherein one or more carbon atoms are replaced by a heteroatom so as to provide an aromatic residue. Preferred heteroaryl have 3-20 ring atoms, e.g. 3-10. Particularly preferred heteroaryl are 5-6 and 9-10 membered bicyclic ring systems. Suitable heteroatoms include, O, N, S, P and Se, particularly O, N and S. Where two or more carbon atoms are replaced, this may be by two or more of the same heteroatom or by different heteroatoms. Suitable examples of heteroaryl groups may include pyridyl, pyrrolyl, thienyl, imidazolyl, furanyl, benzothienyl, isobenzothienyl, benzofuranyl, isobenzofuranyl, indolyl, isoindolyl, pyrazolyl, pyrazinyl, pyrimidinyl, pyridazinyl, indolizinyl, quinolyl, isoquinolyl, phthalazinyl, 1,5-naphthyridinyl, quinozalinyl, quinazolinyl, quinolinyl, oxazolyl, thiazolyl, isothiazolyl, isoxazolyl, triazolyl, oxadialzolyl, oxatriazolyl, triazinyl, and furazanyl. A heteroaryl group may be optionally substituted by one or more optional substituents as herein defined. The term "heteroarylene" is intended to denote the divalent form of heteroaryl.

The term "acyl" either alone or in compound words denotes a group containing the moiety C=O (and not being a carboxylic acid, ester or amide) Preferred acyl includes C(O)—$R^e$, wherein $R^e$ is hydrogen or an alkyl, alkenyl, alkynyl, aryl, heteroaryl, carbocyclyl, or heterocyclyl residue. Examples of acyl include formyl, straight chain or branched alkanoyl (e.g. $C_{1-20}$) such as acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aryloxyalkanoyl such as phenoxyacetyl and phenoxypropionyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolyglyoxyloyl and thienylglyoxyloyl. The $R^x$ residue may be optionally substituted as described herein.

The term "sulfoxide", either alone or in a compound word, refers to a group —S(O)$R^f$ wherein $R^f$ is selected from hydrogen, alkyl, alkenyl, alkynyl, aryl, heteroaryl, heterocyclyl, carbocyclyl, and aralkyl. Examples of preferred $R^f$ include $C_{1-20}$ alkyl, phenyl and benzyl.

The term "sulfonyl", either alone or in a compound word, refers to a group S(O)$_2$—$R^f$, wherein $R^f$ is selected from hydrogen, alkyl, alkenyl, alkynyl, aryl, heteroaryl, heterocyclyl, carbocyclyl and aralkyl. Examples of preferred $R^f$ include $C_{1-20}$ alkyl, phenyl and benzyl.

The term "sulfonamide", either alone or in a compound word, refers to a group S(O)NR$^f$R$^f$ wherein each $R^f$ is independently selected from hydrogen, alkyl, alkenyl, alkynyl, aryl, heteroaryl, heterocyclyl, carbocyclyl, and aralkyl. Examples of preferred $R^f$ include $C_{1-20}$alkyl, phenyl and benzyl. In a preferred embodiment at least one $R^f$ is hydrogen. In another form, both $R^f$ are hydrogen.

The term, "amino" is used here in its broadest sense as understood in the art and includes groups of the formula NR$^a$R$^b$ wherein $R^a$ and $R^b$ may be independently selected from hydrogen, alkyl, alkenyl, alkynyl, aryl, carbocyclyl, heteroaryl, heterocyclyl, arylalkyl, and acyl. $R^a$ and $R^b$, together with the nitrogen to which they are attached, may also form a monocyclic, or polycyclic ring system e.g. a 3-10 membered ring, particularly, 5-6 and 9-10 membered systems. Examples of "amino" include $NH_2$, NHalkyl (e.g. $C_{1-20}$ alkyl), NHaryl (e.g. NHphenyl), NHaralkyl (e.g. NHbenzyl), NHacyl (e.g. NHC(O)$C_{1-20}$ alkyl, NHC(O)phenyl), Nalkylalkyl (wherein each alkyl, for example $C_{1-20}$, may be the same or different) and 5 or 6 membered rings, optionally containing one or more same or different heteroatoms (e.g. O, N and S).

The term "amido" is used here in its broadest sense as understood in the art and includes groups having the formula C(O)NR$^a$R$^b$, wherein $R^a$ and $R^b$ are as defined as above. Examples of amido include C(O)$NH_2$, C(O)NHalkyl (e.g. $C_{1-20}$ alkyl), C(O)NHaryl (e.g. C(O)NHphenyl), C(O)NHaralkyl (e.g. C(O)NHbenzyl), C(O)NHacyl (e.g. C(O)NHC(O)$C_{1-20}$ alkyl, C(O)NHC(O)phenyl), C(O)Nalkylalkyl (wherein each alkyl, for example $C_{1-20}$, may be the same or different) and 5 or 6 membered rings, optionally containing one or more same or different heteroatoms (e.g. O, N and S).

The term "carboxy ester" is used here in its broadest sense as understood in the art and includes groups having the formula CO$_2$R$^g$, wherein $R^g$ may be selected from groups including alkyl, alkenyl, alkynyl, aryl, carbocyclyl, heteroaryl, heterocyclyl, aralkyl, and acyl. Examples of carboxy ester include CO$_2$C$_{1-20}$ alkyl, CO$_2$aryl (e.g. CO$_2$phenyl), CO$_2$aralkyl (e.g. CO$_2$ benzyl).

In this specification "optionally substituted" is taken to mean that a group may or may not be substituted or fused (so as to form a condensed polycyclic group) with one, two, three or more of organic and inorganic groups, including those selected from: alkyl, alkenyl, alkynyl, carbocyclyl, aryl, heterocyclyl, heteroaryl, acyl, aralkyl, alkaryl, alkheterocyclyl, alkheteroaryl, alkcarbocyclyl, halo, haloalkyl, haloalkenyl, haloalkynyl, haloaryl, halocarbocyclyl, haloheterocyclyl, haloheteroaryl, haloacyl, haloaryalkyl, hydroxy, hydroxyalkyl, hydroxyalkenyl, hydroxyalkynyl, hydroxycarbocyclyl, hydroxyaryl, hydroxyheterocyclyl, hydroxyheteroaryl, hydroxyacyl, hydroxyaralkyl, alkoxyalkyl, alkoxyalkenyl, alkoxyalkynyl, alkoxycarbocyclyl, alkoxyaryl, alkoxyheterocyclyl, alkoxyheteroaryl, alkoxyacyl, alkoxyaralkyl, alkoxy, alkenyloxy, alkynyloxy, aryloxy, carbocyclyloxy, aralkyloxy, heteroaryloxy, heterocyclyloxy, acyloxy, haloalkoxy, haloalkenyloxy, haloalkynyloxy, haloaryloxy, halocarbocyclyloxy, haloaralkyloxy, haloheteroaryloxy, haloheterocyclyloxy, haloacyloxy, nitro, nitroalkyl, nitroalkenyl, nitroalkynyl, nitroaryl, nitroheterocyclyl, nitroheteroayl, nitrocarbocyclyl, nitroacyl, nitroaralkyl, amino ($NH_2$), alkylamino, dialkylamino, alkenylamino, alkynylamino, arylamino, diarylamino, aralkylamino, diaralkylamino, acylamino, diacylamino, heterocyclamino, heteroarylamino, carboxy, carboxyester, amido, alkylsulphonyloxy, arylsulphenyloxy, alkylsulphenyl, arylsulphenyl, thio, alkylthio, alkenylthio, alkynylthio, arylthio, aralkylthio, carbocyclylthio, heterocyclylthio, heteroarylthio, acylthio, sulfoxide, sulfonyl, sulfonamide, aminoalkyl, aminoalkenyl, aminoalkynyl, aminocarbocyclyl, aminoaryl, aminoheterocyclyl, aminoheteroaryl, aminoacyl, aminoaralkyl, thioalkyl, thioalkenyl, thioalkynyl, thiocarbocyclyl, thioaryl, thioheterocyclyl, thioheteroaryl, thioacyl, thioaralkyl, carboxyalkyl, carboxyalkenyl, carboxyalkynyl, carboxycarbocyclyl, carboxyaryl, carboxyheterocyclyl, carboxyheteroaryl, carboxyacyl, carboxyaralkyl, carboxyesteralkyl, carboxyesteralkenyl, carboxyesteralkynyl, carboxyestercarbocyclyl, carboxyesteraryl, carboxyesterheterocyclyl, carboxyesterheteroaryl, carboxyesteracyl, carboxyesteraralkyl, amidoalkyl, amidoalkenyl, amidoalkynyl, amidocarbocyclyl, amidoaryl, amidoheterocyclyl, amidoheteroaryl, amidoacyl, amidoaralkyl, formylalkyl, formylalkenyl, formylalkynyl, formylcarbocyclyl, formylaryl, formylheterocyclyl, formylheteroaryl, formylacyl, formylaralkyl, acylalkyl, acylalkenyl, acylalkynyl, acylcarbocyclyl, acylaryl, acylheterocyclyl, acylheteroaryl, acylacyl, acylaralkyl, sulfoxidealkyl, sulfoxidealkenyl, sulfoxidealkynyl, sulfoxidecarbocyclyl, sulfoxidearyl, sulfoxideheterocyclyl, sulfoxideheteroaryl, sulfoxideacyl, sulfoxidearalkyl, sulfonylalkyl, sulfonylalkenyl, sulfonylalkynyl, sulfonylcarbocyclyl, sulfonylaryl, sulfonylheterocyclyl, sulfonylheteroaryl, sulfonylacyl, sulfonylaralkyl, sulfonamidoalkyl, sulfonamidoalkenyl, sulfonamidoalkynyl, sulfonamidocarbocyclyl, sulfonamidoaryl, sulfonamidoheterocyclyl, sulfonamidoheteroaryl, sulfonamidoacyl, sulfonamidoaralkyl, nitroalkyl, nitroalkenyl, nitroalkynyl, nitrocarbocyclyl, nitroaryl, nitroheterocyclyl, nitroheteroaryl, nitroacyl, nitroaralkyl, cyano, sulfate and phosphate groups. Optional substitution may also be taken to refer to where a —$CH_2$— group in a chain or ring is replaced by a group selected from —O—, —S—, —$NR^a$—, —C(O)— (i.e. carbonyl), —C(O)O— (i.e. ester), and —C(O)$NR^a$— (i.e. amide), where $R^a$ is as defined herein.

Preferred optional substituents include alkyl, (e.g. $C_{1-6}$ alkyl such as methyl, ethyl, propyl, butyl, cyclopropyl, cyclobutyl, cyclopentyl or cyclohexyl), hydroxyalkyl (e.g. hydroxymethyl, hydroxyethyl, hydroxypropyl), alkoxyalkyl (e.g. methoxymethyl, methoxyethyl, methoxypropyl, ethoxymethyl, ethoxyethyl, ethoxypropyl etc) alkoxy (e.g. $C_{1-6}$ alkoxy such as methoxy, ethoxy, propoxy, butoxy, cyclopropoxy, cyclobutoxy), halo, trifluoromethyl, trichloromethyl, tribromomethyl, hydroxy, phenyl (which itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), benzyl (wherein benzyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), phenoxy (wherein phenyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), benzyloxy (wherein benzyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), amino, alkylamino (e.g. $C_{1-6}$ alkyl, such as methylamino, ethylamino, propylamino etc), dialkylamino (e.g. $C_{1-6}$ alkyl, such as dimethylamino, diethylamino, dipropylamino), acylamino (e.g. NHC(O)$CH_3$), phenylamino (wherein phenyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), nitro, formyl, —C(O)-alkyl (e.g. $C_{1-6}$ alkyl, such as acetyl), O—C(O)-alkyl (e.g. $C_{1-6}$ alkyl, such as acetyloxy), benzoyl (wherein the phenyl group itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro OC(O)$C_{1-6}$ alkyl, and amino), replacement of $CH_2$ with C=O, $CO_2H$, $CO_2$alkyl (e.g. $C_{1-6}$ alkyl such as methyl ester, ethyl ester, propyl ester, butyl ester), $CO_2$phenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), $CONH_2$, CONHphenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), CONHbenzyl (wherein benzyl itself may be further substituted e.g., by $C_{1-6}$ alkyl, halo, hydroxy hydroxyl $C_{1-6}$ alkyl, $C_{1-6}$ alkoxy, halo $C_{1-6}$ alkyl, cyano, nitro OC(O)$C_{1-6}$ alkyl, and amino), CONHalkyl (e.g. $C_{1-6}$ alkyl such as methyl ester, ethyl ester, propyl ester, butyl amide) CONHdialkyl (e.g. $C_{1-6}$ alkyl) aminoalkyl (e.g., HN$C_{1-6}$ alkyl-, $C_{1-6}$ alkylHN—$C_{1-6}$ alkyl- and ($C_{1-6}$ alkyl)$_2$N—$C_{1-6}$ alkyl-), thioalkyl (e.g., HS $C_{1-6}$ alkyl-), carboxyalkyl (e.g., $HO_2CC_{1-6}$ alkyl-), carboxyesteralkyl (e.g., $C_{1-6}$ alkyl$O_2CC_{1-6}$ alkyl-), amido alkyl (e.g., $H_2N(O)CC_{1-6}$ alkyl-, H($C_{1-6}$ alkyl)N(O)C$C_{1-6}$ alkyl-), formylalkyl (e.g., OHC$C_{1-6}$ alkyl-), acylalkyl (e.g., $C_{1-6}$ alkyl(O)C$C_{1-6}$ alkyl-), nitroalkyl (e.g., $O_2NC_{1-6}$ alkyl-), sulfoxidealkyl (e.g., R(O)S$C_{1-6}$ alkyl, such as $C_{1-6}$alkyl(O)S$C_{1-6}$ alkyl-), sulfonylalkyl (e.g., R(O)$_2$S$C_{1-6}$ alkyl-such as $C_{1-6}$ alkyl(O)$_2$S$C_{1-6}$ alkyl-), sulfonamidoalkyl (e.g., $_2$HRN(O)S$C_{1-6}$ alkyl, H($C_{1-6}$ alkyl)N(O)S$C_{1-6}$ alkyl-).

The term "heteroatom" or "hetero" as used herein in its broadest sense refers to any atom other than a carbon atom which may be a member of a cyclic organic group. Particular examples of heteroatoms include nitrogen, oxygen, sulfur, phosphorous, boron, silicon, selenium and tellurium, more particularly nitrogen, oxygen and sulfur.

For monovalent substituents, terms written as "[groupA] [group B]" refer to group A when linked by a divalent form of group B. For example, "[group A] [alkyl]" refers to a particular group A (such as hydroxy, amino, etc.) when linked by divalent alkyl, i.e. alkylene (e.g. hydroxyethyl is intended to denote HO—CH$_2$—CH—). Thus, terms written as "[group]oxy" refer to a particular group when linked by oxygen, for example, the terms "alkoxy" or "alkyloxy", "alkenoxy" or "alkenyloxy", "alkynoxy" or "alkynyloxy", "aryloxy" and "acyloxy", respectively, denote alkyl, alkenyl, alkynyl, aryl and acyl groups as hereinbefore defined when linked by oxygen. Similarly, terms written as "[group]thio" refer to a particular group when linked by sulfur, for example, the terms "alkylthio", "alkenylthio", alkynylthio" and "arylthio", respectively, denote alkyl, alkenyl, alkynyl and aryl groups as hereinbefore defined when linked by sulfur.

The following invention will hereinafter be described with reference to the following non-limiting examples.

EXAMPLES

Example 1

Production of Perfluoropolyether Methacrylate and Oligo (Ethylene Glycol) Methyl Ether Acrylate Copolymers (Formula 1); where Perfluoropolyether is Pendant to the Backbone.

The Title Compound was Synthesized as Follows:
Synthesis of Perfluoropolyether Methacrylate (PFPEMA)

Figure 2:
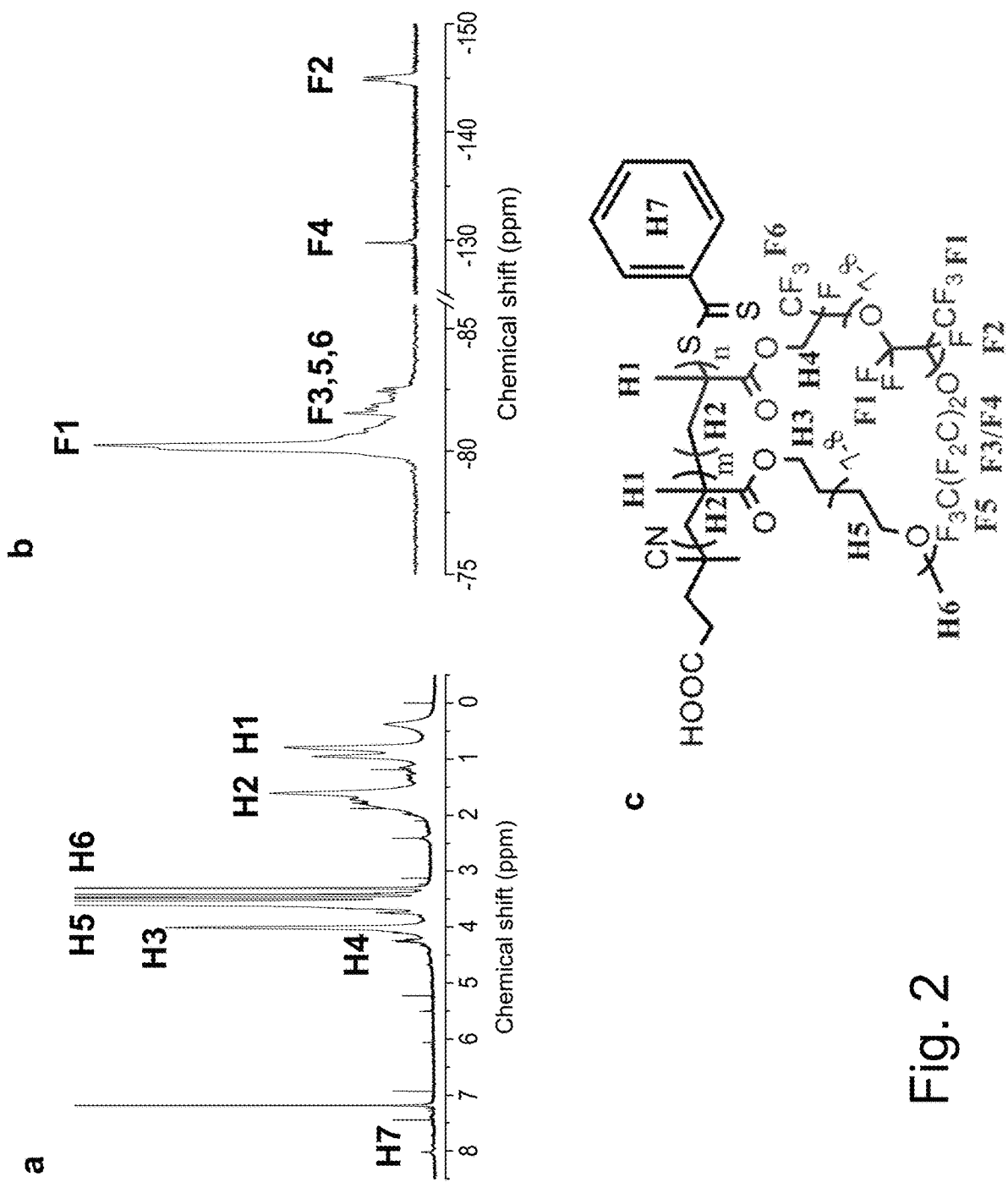
FIG. 2 illustrates (a) $^1$H and (b) $^{19}$F NMR spectra in CDCl$_3$ and assignments to the spectra of the poly(OEGMA-co-PFPEMA) according to Example 1. (c) The chemical structure of the poly(OEGMA-co-PFPEMA) showing labels for assignment of the NMR spectra.

Into a two-neck flask fitted with a dropping funnel, stirrer bar and purged with N$_2$, monohydroxy-terminated perfluoropolyether (PFPE-ol) (1.65 kDa, 2.0 g, 1.21 mmol), triethylamine (211 µL, 0.153 g, 1.52 mmol), 2,6-di-t-butyl-4-methylphenol (20 mg) in α,α,α-trifluorotoluene (2 mL) (TFT) were added. Methacryloyl chloride (142 µL, 0.152 g, 1.45 mmol) was added dropwise at 0° C., stirred for 1 h at this temperature, and then allowed to warm to room temperature overnight. The mixture was then diluted with TFT (20 mL), poured into water (50 mL) and the organic phase was washed with HCl (5%, 2×50 mL), NaOH (2×50 mL) and water to neutrality followed by drying over MgSO$_4$. The product was collected by filtration through a sintered glass funnel, before being reduced to dryness under vacuum (0.1 mmHg). The perfluoropolyether methacrylate (PFPEMA), a colorless oil, was treated with another portion of 2,6-di-t-butyl-4-methylphenol (20 mg), sealed under N$_2$ and stored below 5° C. The resultant polymer was characterised by solution-state $^1$H and $^{19}$F NMR (FIG. 2).

Production of Perfluoropolyether Methacrylate and Oligo (Ethylene Glycol) Methyl Ether Acrylate Copolymers Through RAFT Polymerization The copolymerization of OEGMA and PFPEMA was conducted as follows. In a typical experiment, OEGMA (1.2 g, 5 mmol), PFPEMA (1.73 g, 1 mmol), V40 (4.89 mg, 0.02 mmol), and CPADB (27.9 mg, 0.1 mmol) were dissolved in 5 mL TFT and sealed in a 25 mL flask fitted with a magnetic stirrer bar. The solution was then deoxygenated by purging thoroughly with nitrogen for 15 min, heated to 90° C. in an oil bath, and allowed to react for 24 h. The resulting solution was centrifuged for 5 min at 4000 rpm and the supernatant was precipitated into hexane and dissolved in THF three times. The precipitate was then dissolved in water and purified by dialysis, yielding a pink viscous solid after freeze drying.

Example 2

Production of Chain-End Functionalized Perfluoropolyether Polymers with Perfluoropolyether in the Backbone (Formula 2)

The Title Compound was Synthesized as Follows:

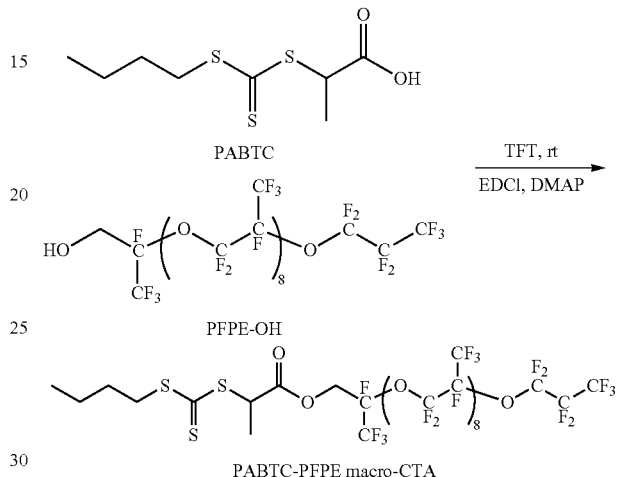

Synthesis of Macro RAFT Agent 2-(Butylthiocarbonothioylthio)Propionic Acid-Perfluoropolyether The 2-(butylthiocarbonothioylthio)propionic acid-perfluoropolyether (PABTC-PFPE) macro-RAFT agent was prepared by the EDCI/DMAP catalyzed esterification of carboxylic acid from PABTC RAFT agent with PFPE-OH. A solution of N-(3-dimethylaminopropyl)-N'-ethylcarbodiimide hydrochloride (EDCI) (0.288 g, 1.50 mmol) in trifluorotoluene (TFT, 5 mL) was added dropwise to a solution of PFPEs (1.7 g, 1.0 mmol), 2-(butylthiocarbonothioylthio)propionic acid (PABTC, 0.381 g, 1.60 mmol) and 4-dimethyl aminopyridine (DMAP, 0.019 g, 0.16 mmol) in TFT (10 mL) at 0° C. After complete addition, the reaction mixture was allowed to stir for 20 hours at room temperature. The reaction mixture was washed twice with a 1 M sodium hydroxide solution then twice with distilled water. The organic layer was dried over anhydrous magnesium sulfate, filtered, concentrated under vacuum and subjected to precipitation against methanol to remove the unreacted PABTC RAFT agent. The desired fraction was concentrated under vacuum to afford the product as a yellow oil.

Production of Chain-End Functionalized Perfluoropolyether Polymers Through RAFT Polymerization PABTC-PFPE macro-RAFT agent (187 mg, 0.11 mmol), OEGA (960 mg, 2 mmol) and AIBN (3.28 mg, 0.02 mmol) were dissolved in TFT (2 mL) and sealed in a 10 mL flask fitted with a magnetic stirrer bar. The solution was then deoxygenated by purging thoroughly with nitrogen for 15 min, heated to 65° C. in an oil bath, and allowed to react for 12 h. Upon completing the reaction, the solution was precipitated into hexane and dissolved in THF three times. The precipitate was then dissolved in water and purified by dialysis for two days (molecular weight cut-off of 2000 or 3500 Da), yielding a yellow viscous solid after freezer drying. Polymers with a range of compositions were prepared under identical conditions apart from differences in the initial feed amount of OEGA.

Figure 3:
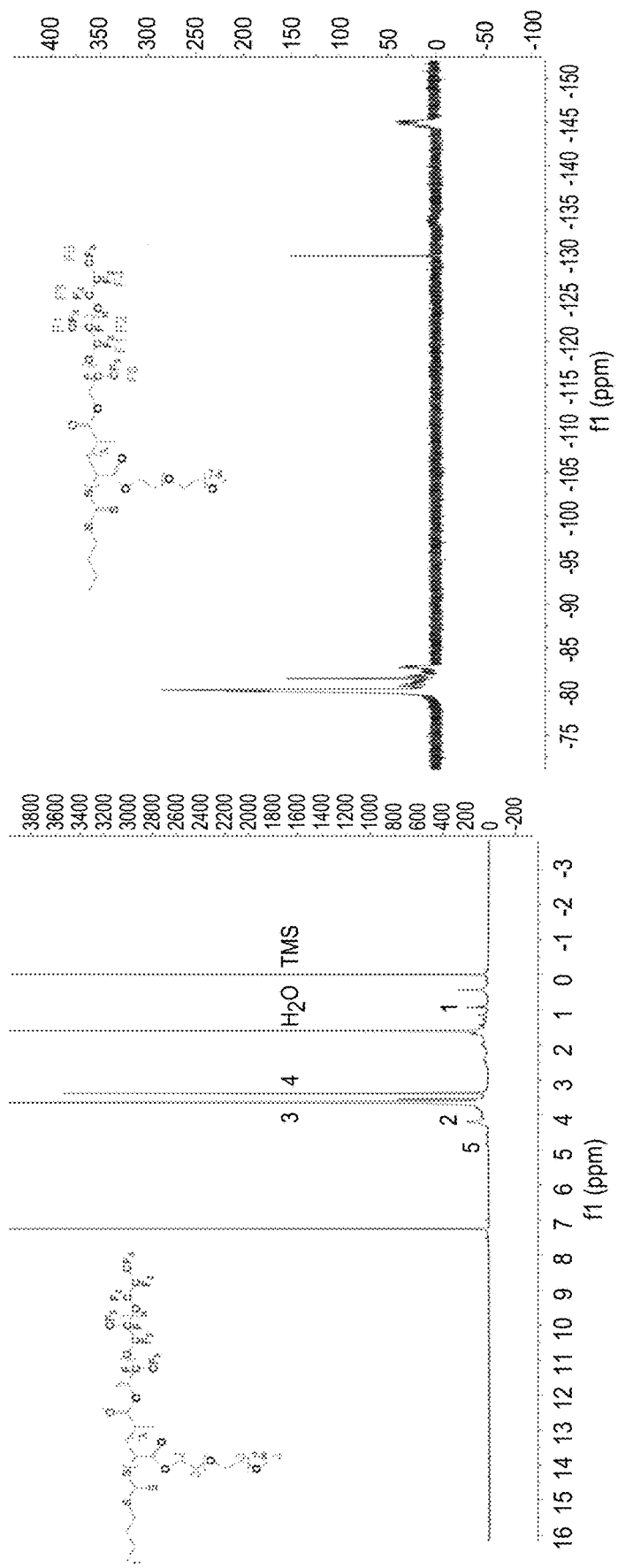
FIG. 3 illustrates $^1$H (left) and $^{19}$F NMR (right) spectra in CDCl$_3$ and assignments to the spectra of the chain-end functionalized perfluoropolyether polymer according to Example 2.

$^1$H and $^{19}$F NMR spectra of the chain-end functionalized perfluoropolyether polymer confirmed the chemical structure (FIG. 3).

Figure 4:
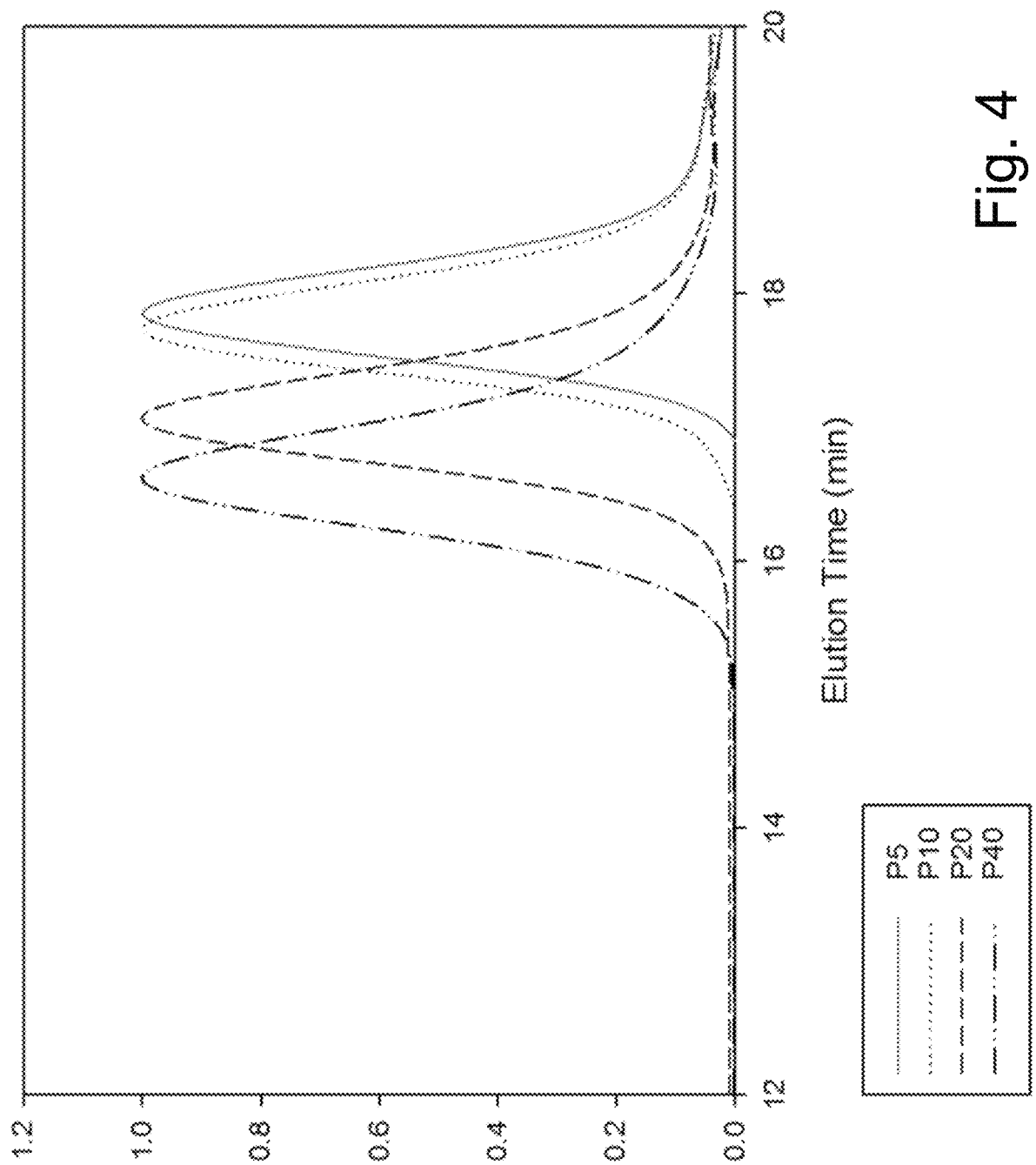
FIG. 4 illustrates SEC traces of the four block copolymers with 5-40 OEGA units according to Example 2.

The ratio of PABTC-PFPE macro-RAFT agent to hydrophilic monomer OEGA can be varied so as to produce block copolymer of varying weight ratios of PFPE to hydrophilic block. In this example, the ratio of OEGA to macro-RAFT agent was varied to produce block copolymers having OEGA blocks with on average 5, 10, 20 or 40 OEGA units. The SEC traces (FIG. 4) demonstrate an increase in hydrodynamic volume with increasing length of the OEGA block.

Example 3

Adsorption of PFOA by the Chain-End Functionalized Perfluoropolyether Polymers (Formula 2)

Figure 5:
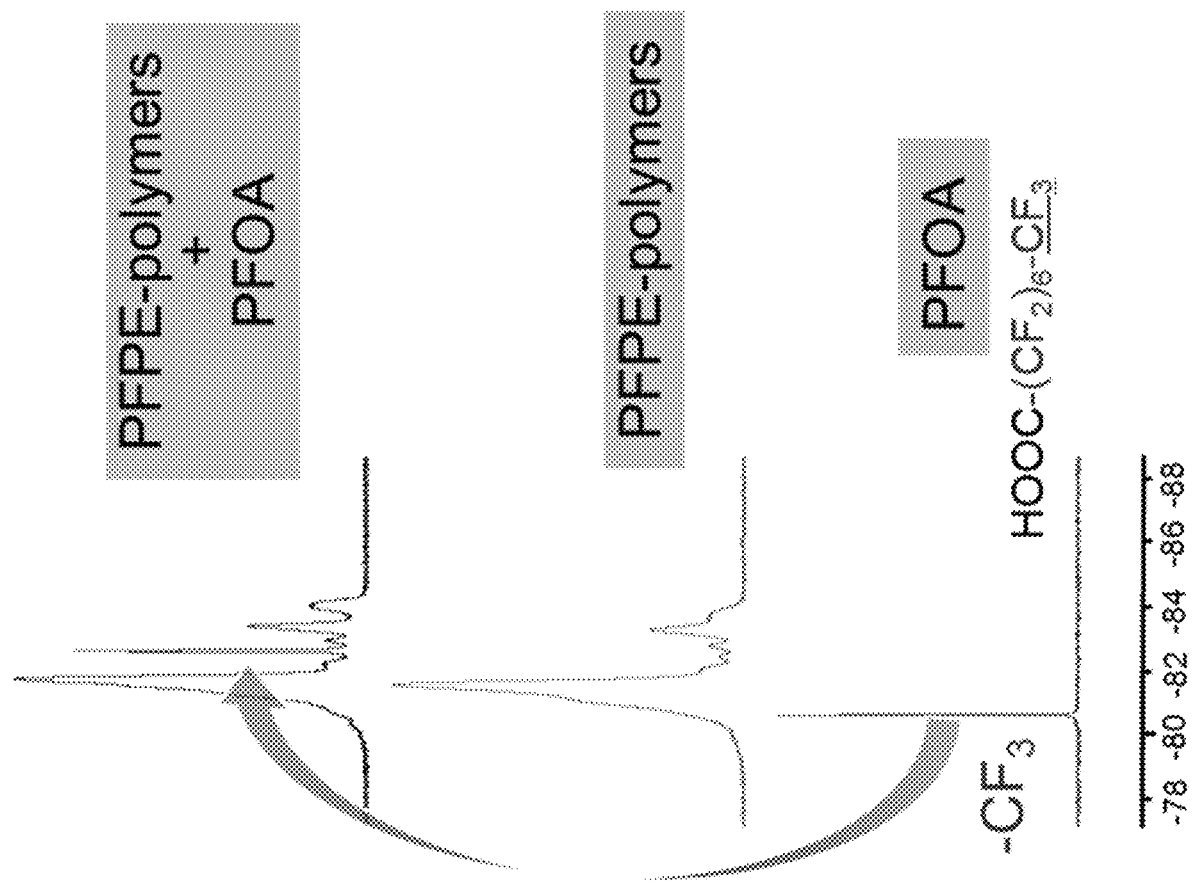
FIG. 5 illustrates $^{19}$F NMR spectra of perfluorooctanoic acid (PFOA), a fluoropolyether block copolymer and after mixing the two solutions together according to Example 3.
Figure 6:
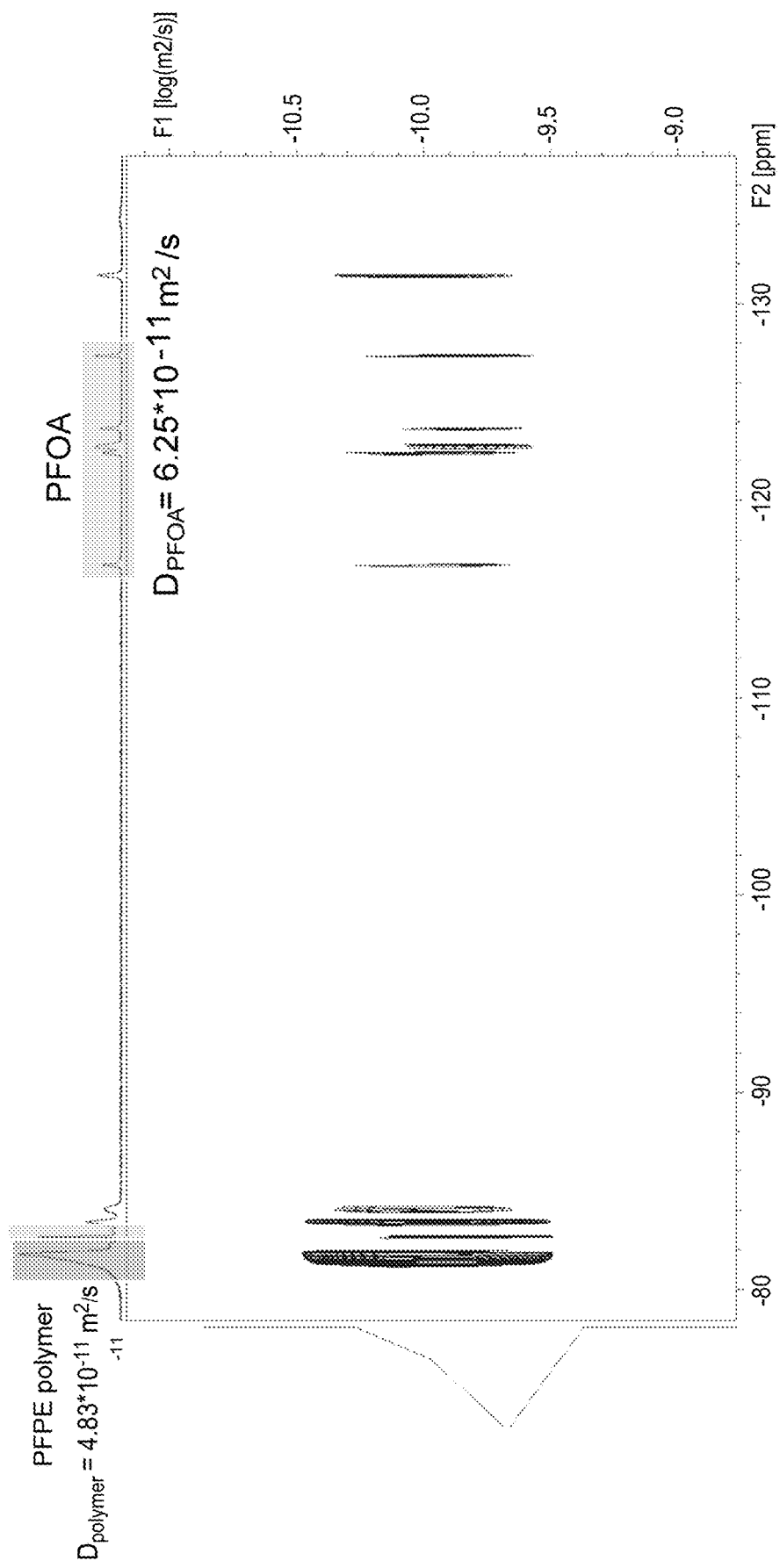
FIG. 6 illustrates $^{19}$F Diffusion-Ordered Spectroscopy of a fluoropolyether block copolymer after absorbing PFOA according to Example 3.

20 mg of PFPE polymer was dissolved in 1 mL of PBS buffer solution (~4.9 mM). Different amount of PFOA (0.8, 1.6, 3.2, 6.4, 12.8, 25.6 and 51.2 mM) was added into the polymer solution. After that, 450 uL of the mixed solution was mixed with 50 uL of D$_2$O for NMR tests. $^{19}$F 1D NMR spectra and $^{19}$F diffusion-ordered spectroscopy were conducted. An example (4.9 mM polymer with 3.2 mM PFOA) of typical 1D $^1$H NMR and DOSY NMR spectra are shown in FIG. 5 and FIG. 6. The change in chemical shift in the 1D NMR spectrum indicates complete absorption of the PFOA by the PFPE polymer. No free (non-absorbed) PFOA is evident in the spectrum. The DOSY NMR experiment confirmed that the PFOA and the polymer diffuse at the same rate, and so the PFOA is within the PFPE polymer particles.

Figure 7:
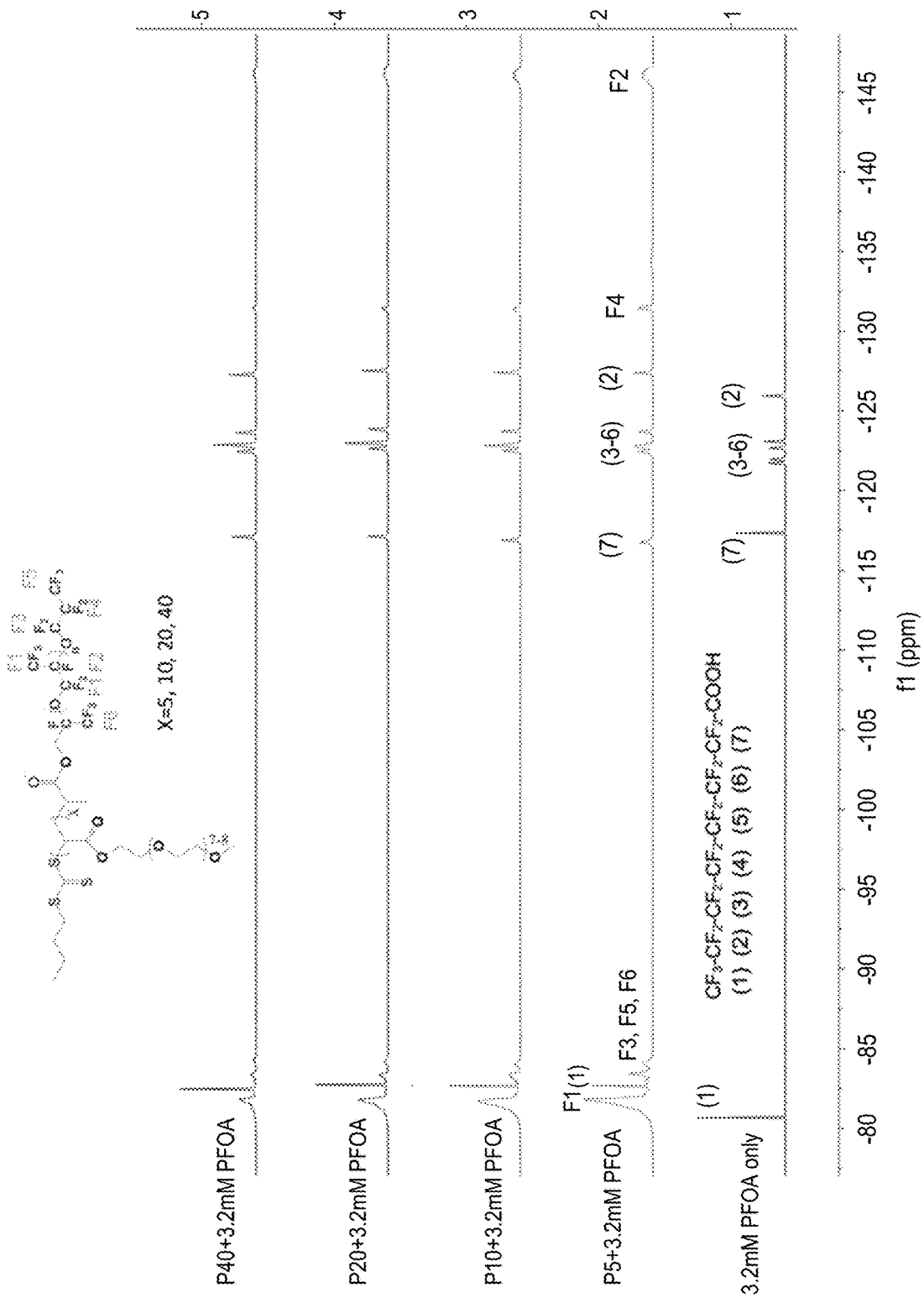
FIG. 7 illustrates $^{19}$F NMR spectra of P5, P10, P20 and P40 in the presence of 3.2 mM of PFOA according to Example 3.

Block copolymer having different ratios of perfluoropolyether to hydrophilic block were capable of removing PFOA from solution (FIG. 7).

Example 4

Adsorption of 1H,1H,2H,2H-Perfluorodecanethiol (PFDT) by the Chain-End Functionalized Perfluoropolyether Polymers (Formula 2)

Figure 8:
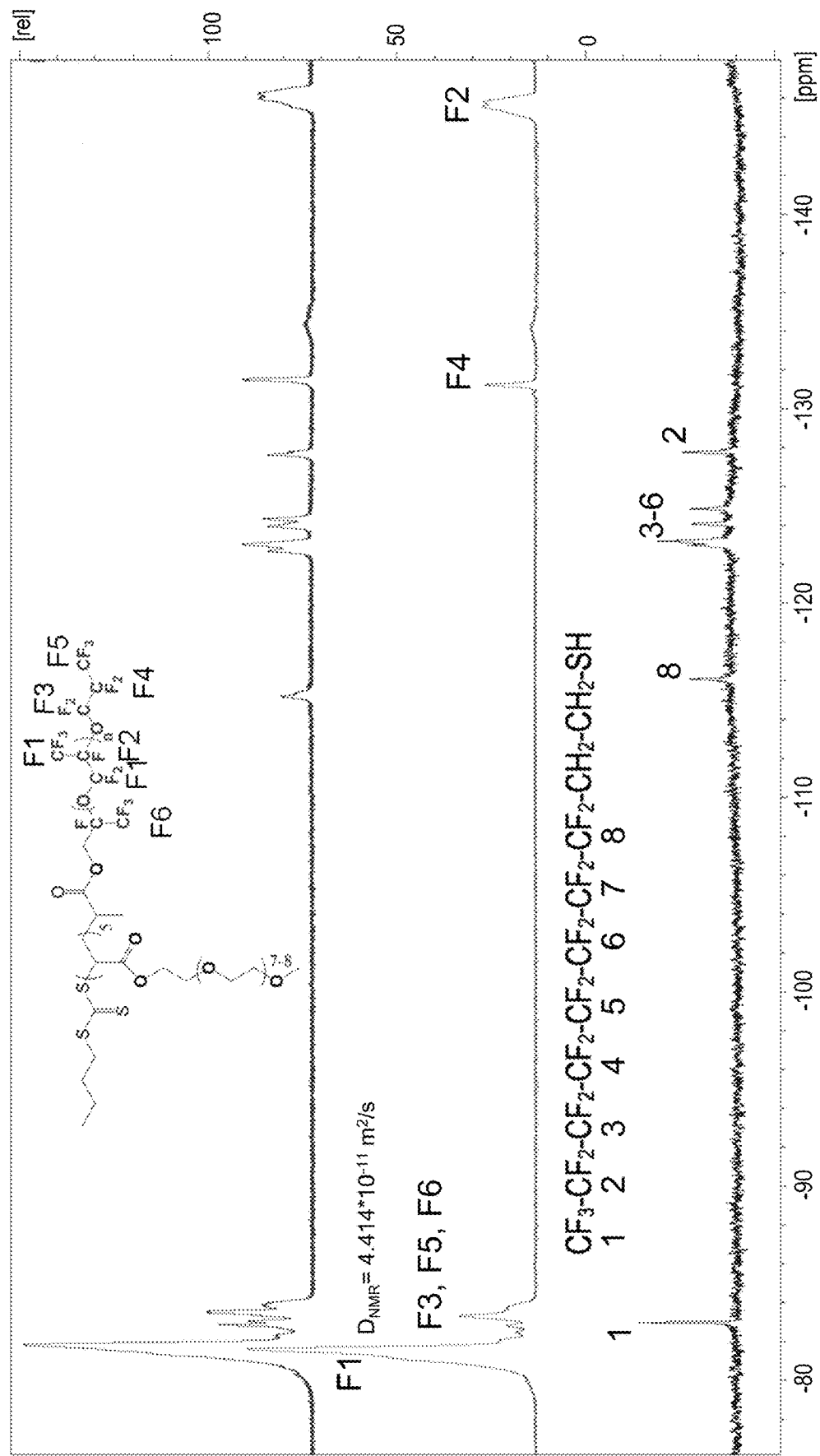
FIG. 8 illustrates $^{19}$F NMR spectra of polymer, 1H,1H,2H,2H-perfluorodecanethiol and 1H,1H,2H,2H-perfluorodecanethiol in the presence of polymer (90% water+10% D$_2$O+ salt). Blue (bottom), 3.2 mM of 1H,1H,2H,2H-perfluorodecanethiol dissolved in PBS without polymer; Green (middle), polymer only; Red (top), 3.2 mM of 1H,1H,2H,2H-perfluorodecanethiol dissolved in 1 mL PBS in the presence of 20 mg/mL polymer according to Example 4.

20 mg of PFPE polymer was dissolved in 1 mL of PBS buffer solution (~4.9 mM). An amount of 1H,1H,2H,2H-Perfluorodecanethiol (PFDT) (3.2 mM) was added to the polymer solution. After that, 450 uL of the mixed solution was mixed with 50 uL of D$_2$O for NMR tests. The observed changes in chemical shift (FIG. 8) and the measurements of diffusion coefficient confirmed efficient uptake of the PFDT by the block copolymer.

Example 5

Adsorption of Perfluorinated Crown Ether (PFCE) by the Chain-End Functionalized Perfluoropolyether Polymers (Formula 2)

Figure 9:
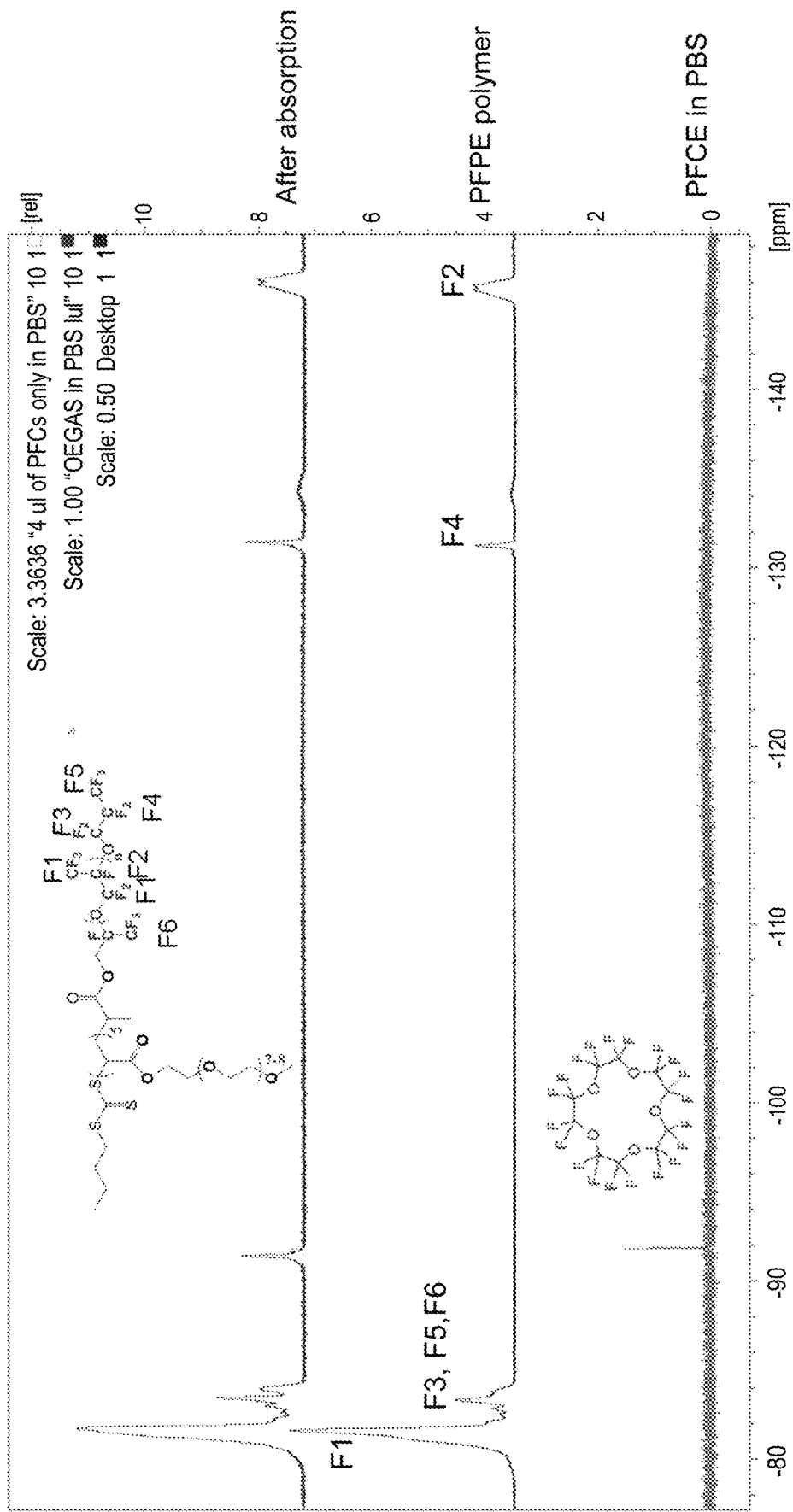
FIG. 9 illustrates $^{19}$F NMR spectra of P5, perfluoro-15-crown-5-ether (PFCE) and perfluoro-15-crown-5-ether in the presence of polymer (90% water+10% D$_2$O+ salt). Green (bottom), 3.2 mM of perfluoro-15-crown-5-ether dissolved in PBS without polymer; Blue (middle), polymer only; Red (top), 3.2 mM of perfluoro-15-crown-5-ether dissolved in 1 mL PBS in the presence of 20 mg/mL polymer according to Example 5.

20 mg of PFPE polymer was dissolved in 1 mL of PBS buffer solution (~4.9 mM). An amount of perfluoro-15-crown-5-ether (PFCE) (3.2 mM) was added to the polymer solution. After that, 450 uL of the mixed solution was mixed with 50 uL of D$_2$O for NMR tests. The observed changes in chemical shift (FIG. 9) and the measurements of diffusion coefficient confirmed efficient uptake of the PFCE by the block copolymer.

Example 6

Adsorption of GenX Salt by the Chain-End Functionalized Perfluoropolyether Polymers (Formula 2)

Figure 10:
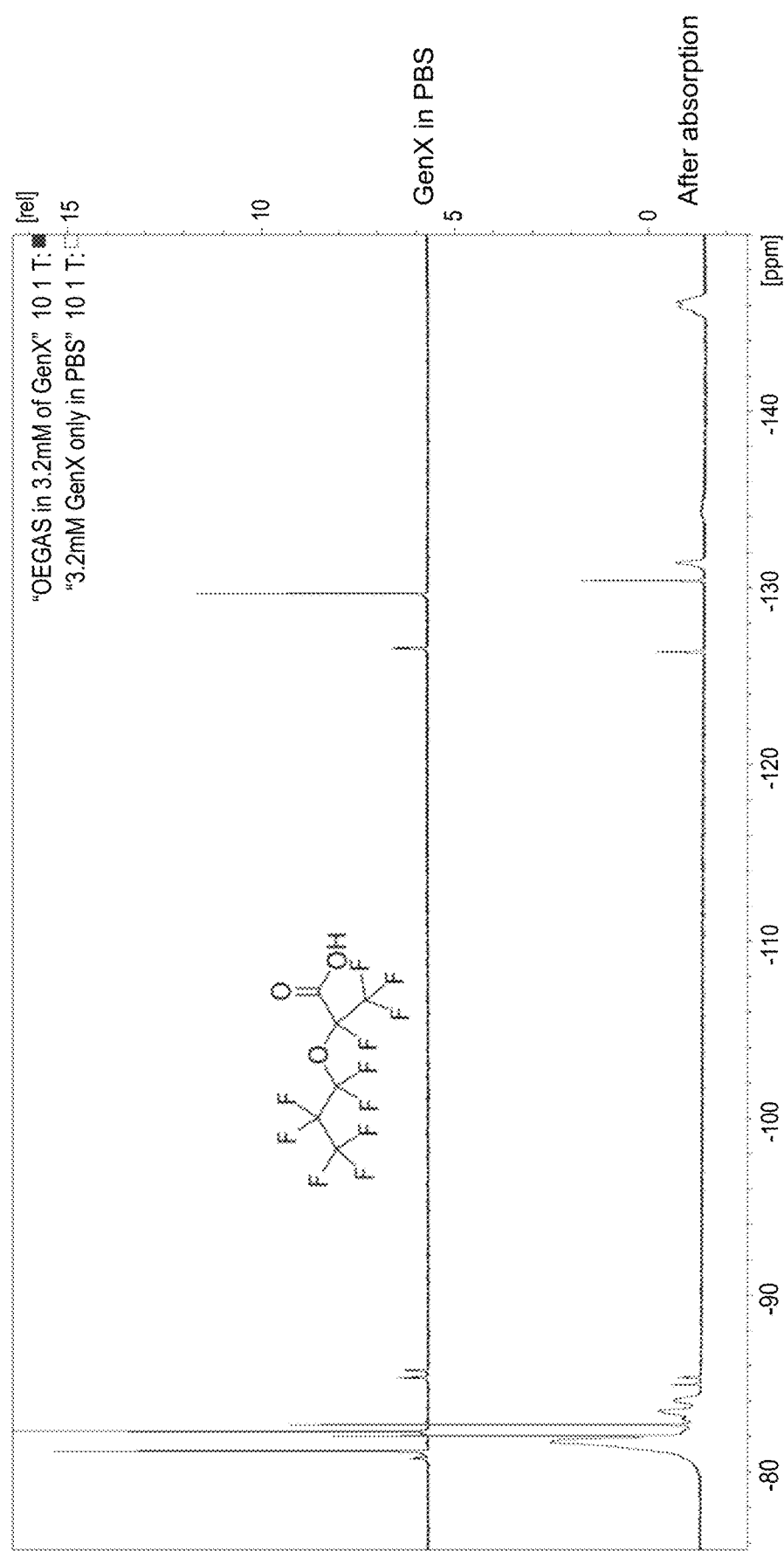
FIG. 10 illustrates $^{19}$F NMR spectra of GenX salt only and GenX in the presence of polymer (90% water+10% D$_2$O+ salt). Blue (top), 3.2 mM of GenX dissolved in PBS without polymer; Red (bottom), 3.2 mM of GenX salt dissolved in 1 mL PBS in the presence of 20 mg/mL polymer according to Example 6.

20 mg of PFPE polymer was dissolved in 1 mL of PBS buffer solution (~4.9 mM). An amount of perfluoro-15-crown-5-ether (PFCE) (3.2 mM) was added to the polymer solution. After that, 450 uL of the mixed solution was mixed with 50 uL of D$_2$O for NMR tests. The observed changes in chemical shift (FIG. 10) confirmed efficient removal of the PFCE by the block copolymer.

Example 7

Adsorption of PFOA from Whole Blood by the Chain-End Functionalized Perfluoropolyether Polymers (Formula 2)

Figure 11:
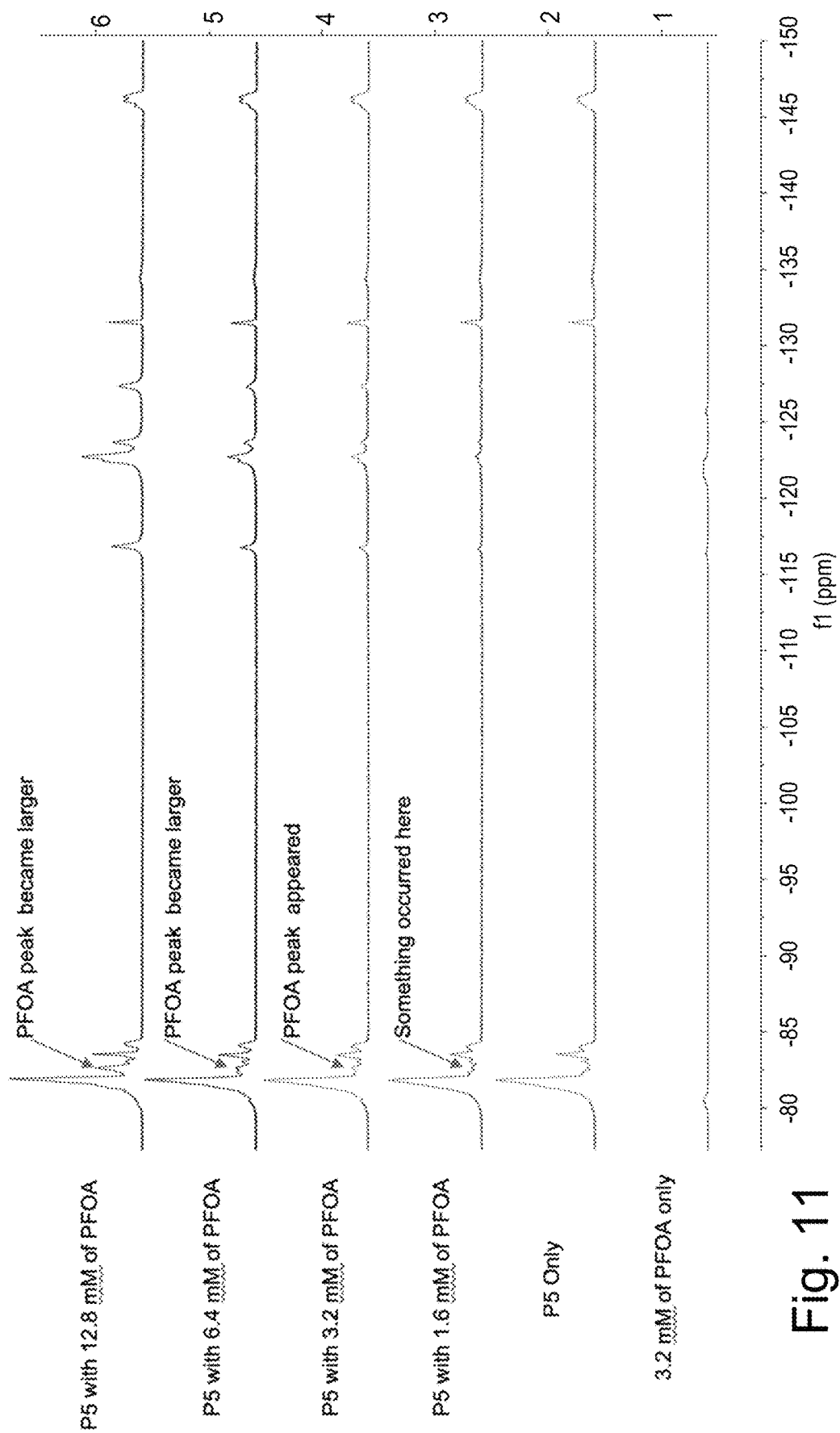
FIG. 11 illustrates $^{19}$F NMR spectra of different concentrations of PFOA mixed with PFPE block copolymer in rat blood. The polymer concentration was 20 mg/L according to Example 7.

A solution of 20 mg/mL of PFPE block copolymer in rat blood was prepared, and increasing amounts of PFOA added to the solution. The 19F NMR spectra in Figure ABC show chemical shifts of the PFOA consistent with encapsulation, and there is no evidence of interaction with the blood components. The PFPE block copolymer is able to remove the PFOA from the rat blood (FIG. 11).

Example 8

Separation of the Block Copolymer and the Fluorinated Carbon Compound (PFOA)

Figure 12:
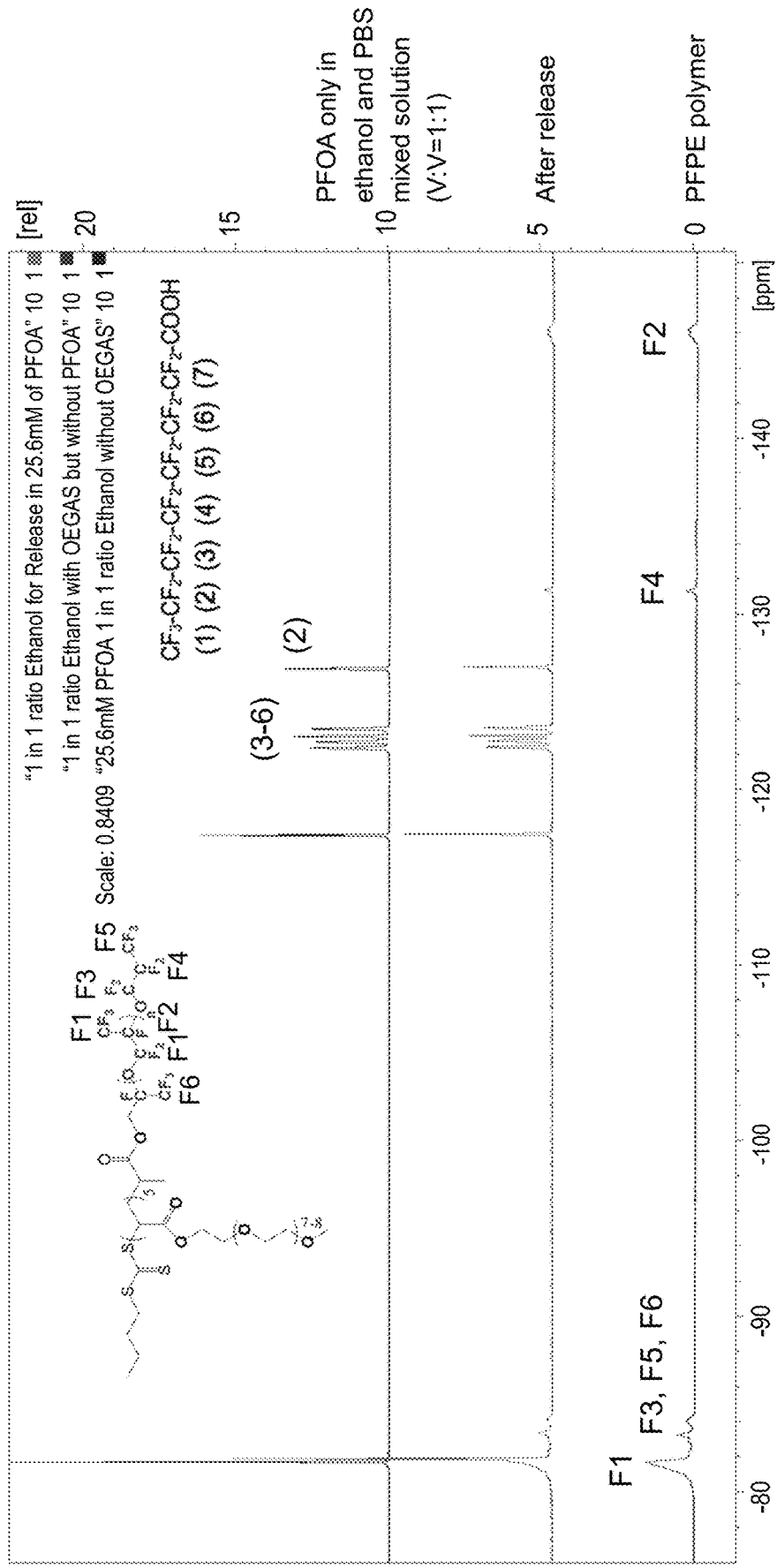
FIG. 12 illustrates $^{19}$F NMR spectra of polymer, PFOA only and PFOA in the presence of polymer after adding ethanol (45% ethanol+45% PBS+10% D$_2$O). Red (bottom), polymer only; Green (middle), after adding ethanol into solution containing polymer and 25.6 mM of PFOA ($V_{ethanol}/V_{solution}$=1:1); Blue (top), 25.6 mM PFOA dissolved in a mixed solution containing ethanol and PBS (V/V=1:1) according to Example 8.

The PFOA absorbed in the block copolymer from aqueous solution could be readily removed by addition of ethanol to the aqueous solution. The solution of PFPE block copolymer and absorbed PFOA in PBS was diluted by an equal volume of ethanol. The $^{19}$F NMR spectrum (Figure ABC) of the PFPE block copolymer+PFOA in ethanol/water (V/V=1:1) shows peaks with chemical shifts identical to the PFOA in an equivalent ethanolic solution i.e. without added PFPE block copolymer (FIG. 12). This indicates no interaction of the PFOA with the block copolymer, i.e. the PFOA has passed into the liquid phase.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A method of capturing a fluorinated carbon compound located within a liquid, the method comprising contacting the fluorinated carbon compound with a block copolymer having a backbone comprising a hydrophilic block and a fluoropolyether block such that the fluorinated carbon compound binds to and is captured by the block copolymer;

removing the fluorinated carbon compound from the liquid by separating from the liquid the block copolymer having the fluorinated carbon compound bound thereto; and separating the fluorinated carbon compound from the block copolymer using an organic solvent and/or heat.

2. The method according to claim 1, wherein the fluoropolyether block presents polyether functionality in the block copolymer backbone.

3. The method according to claim 1, wherein the fluoropolyether block presents polyether functionality pendant to the block copolymer backbone.

4. The method according to claim 1, wherein the hydrophilic block presents hydrophilic functionality in the block copolymer backbone.

5. The method according to claim 1, wherein the hydrophilic block presents hydrophilic functionality pendant to the block copolymer backbone.

6. The method according to claim 1, wherein the fluoropolyether block is a perfluoropolyether block.

7. The method according to claim 1, wherein the liquid is an aqueous liquid.

8. The method according to claim 7, wherein the aqueous liquid is waste water.

9. The method according to claim 1, wherein the liquid is a blood product.

10. The method according to claim 1, wherein the hydrophilic block comprises a polyoxyalkylene moiety.

11. The method according to claim 10, wherein the polyoxyalkylene moiety comprises an oxyalkylene group of formula: $-O(CR^XR^Y)_i-$, where $R^X$ and $R^Y$ are each independently selected from hydrogen and optionally substituted alkyl, and i is an integer ranging from 1 to 10.

12. The method according to claim 1, wherein the fluoropolyether block comprises a moiety selected from $-(C_pF_{2p}O)-$, $-(CF(Z)O)-$, $-(CF(Z)C_pF_{2p}O)-$, $-(C_pF_{2p}CF(Z)O)-$, $-CF_2CF(Z)O)-$, or a combination thereof, where p is an integer ranging from 1 to 10, and where Z is selected from a fluoroalkyl group, a fluoroether group, a fluoropolyether group, or a fluoroalkoxy group.

13. The method according to claim 12, wherein Z is selected from a perfluoroalkyl group, a perfluoroether group, a perfluoropolyether group, or a perfluoroalkoxy group.

14. The method according to claim 1, wherein the fluoropolyether block comprises a moiety selected from $C_3F_7O(CF(CF_3)CF_2O)_nCF(CF_3)-$, $C_3F_7O(CF_2CF_2CF_2O)_nCF_2CF_2-$, and $CF_3O(C_2F_4O)_nCF_2-$, where n has an average value of 1 to 50, for example 3 to 30, 3 to 15, or 3 to 10.

15. The method according to claim 1, wherein the block copolymer has a number average molecular weight ranging from about 1500 to about 110,000 g/mol.

16. The method according to claim 1, wherein the hydrophilic block has a number average molecular weight ranging from 1000 about to about 100,000 g/mol.

17. The method according to claim 1, wherein the hydrophilic block has a number average molecular weight ranging from about 500 to about 10,000 g/mol.

18. The method according to claim 1, wherein the block copolymer is covalently bound to a solid substrate.

19. The method according to claim 1, wherein the block copolymer presents in the form of an aggregate of two or more block copolymer chains.

20. The method of claim 1, wherein the block copolymer comprises a structure of Formula (I), (II) or (III):

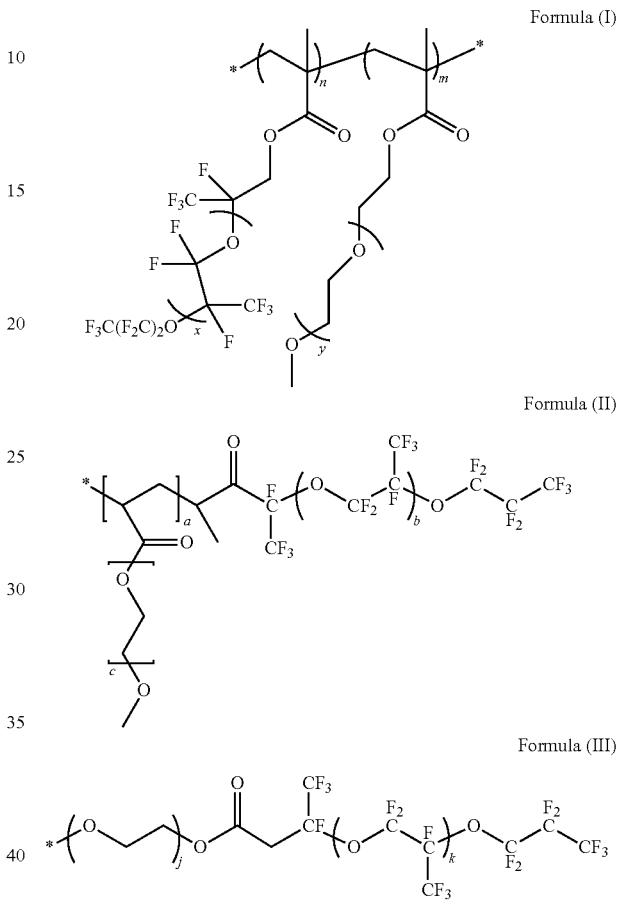

where-in formula (I), n is an integer ranging from 1 to about 30, m is an integer ranging from 1 to about 1000, x is an integer ranging from 1 to about 100 and y is an integer ranging from 1 to about 1000; in formula (II) a is an integer ranging from 1 to about 40, b is an integer ranging from 1 to about 100 and c is an integer ranging from 1 to about 1000; in formula (III) j is an integer ranging from 1 to about 1000 and k is an integer ranging from 1 to about 100; and wherein formulas (I), (II) and (III) * represents a connection point to the block co-polymer.

21. The method according to claim 1, wherein the liquid having the fluorinated carbon compound located therein is obtained by a process comprising contacting a liquid with solid matter comprising fluorinated carbon compound.

* * * * *